US012599611B2

(12) United States Patent
Rabinowicz et al.

(10) Patent No.: US 12,599,611 B2
(45) Date of Patent: Apr. 14, 2026

(54) METHODS AND COMPOSITIONS FOR TREATING SEIZURE DISORDERS IN PEDIATRIC PATIENTS

(71) Applicant: Neurelis, Inc., San Diego, CA (US)

(72) Inventors: Adrian L. Rabinowicz, San Diego, CA (US); Enrique J. Carrazana, San Diego, CA (US)

(73) Assignee: Neurelis, Inc., San Diego, CA (US)

(*) Notice: Subject to any disclaimer, the term of this patent is extended or adjusted under 35 U.S.C. 154(b) by 0 days.

(21) Appl. No.: 17/837,198

(22) Filed: Jun. 10, 2022

(65) Prior Publication Data

US 2022/0401456 A1 Dec. 22, 2022

Related U.S. Application Data

(60) Provisional application No. 63/209,092, filed on Jun. 10, 2021.

(51) Int. Cl.

*A61K 31/5513* (2006.01)
*A61K 9/00* (2006.01)
*A61K 31/355* (2006.01)
*A61K 31/7016* (2006.01)

(52) U.S. Cl.

CPC .......... *A61K 31/5513* (2013.01); *A61K 9/008* (2013.01); *A61K 31/355* (2013.01); *A61K 31/7016* (2013.01)

(58) Field of Classification Search

CPC .. A61K 31/5513; A61K 9/008; A61K 31/355; A61K 31/7016; A61K 47/22; A61K 9/0043; A61K 9/08; A61K 47/10; A61K 47/26

See application file for complete search history.

(56) References Cited

U.S. PATENT DOCUMENTS

| | | | |
|---|---|---|---|
| 3,102,116 | A | 8/1963 | Chase et al. |
| 3,109,843 | A | 11/1963 | Reeder et al. |
| 3,136,815 | A | 6/1964 | Reeder et al. |
| 3,243,427 | A | 3/1966 | Reeder et al. |
| 3,296,249 | A | 1/1967 | Bell |
| 3,299,053 | A | 1/1967 | Archer et al. |
| 3,340,253 | A | 9/1967 | Reeder et al. |
| 3,371,085 | A | 2/1968 | Reeder et al. |
| 3,374,225 | A | 3/1968 | Reeder et al. |
| 3,547,828 | A | 12/1970 | Mansfield et al. |
| 3,567,710 | A | 3/1971 | Fryer et al. |
| 3,609,145 | A | 9/1971 | Moffett |
| 3,722,371 | A | 3/1973 | Boyle |
| 3,849,341 | A | 11/1974 | Lamberti |
| 3,949,072 | A | 4/1976 | Tenta |
| 3,987,052 | A | 10/1976 | Hester, Jr. |
| 4,130,709 | A | 12/1978 | Nagarajan |
| 4,280,957 | A | 7/1981 | Walser et al. |
| 4,397,951 | A | 8/1983 | Taki et al. |
| 4,440,675 | A | 4/1984 | Braude |
| 4,608,278 | A | 8/1986 | Frank et al. |
| 4,657,901 | A | 4/1987 | Ueda et al. |
| 4,690,952 | A | 9/1987 | Kagatani et al. |
| 4,748,158 | A | 5/1988 | Biermann et al. |
| 4,826,689 | A | 5/1989 | Violanto et al. |
| 4,868,289 | A | 9/1989 | Magnusson et al. |
| 4,921,838 | A | 5/1990 | Catsimpoolas et al. |
| 4,973,465 | A | 11/1990 | Baurain et al. |
| 4,997,454 | A | 3/1991 | Violante et al. |
| 5,091,188 | A | 2/1992 | Haynes |
| 5,100,591 | A | 3/1992 | Leclef et al. |
| 5,118,528 | A | 6/1992 | Fessi et al. |
| 5,122,187 | A | 6/1992 | Schwarz et al. |
| 5,145,684 | A | 9/1992 | Liversidge et al. |
| 5,182,258 | A | 1/1993 | Chiou |
| 5,188,837 | A | 2/1993 | Domb |
| 5,192,528 | A | 3/1993 | Radhakrishnan et al. |
| 5,198,420 | A | 3/1993 | Donahoe et al. |
| 5,236,707 | A | 8/1993 | Stewart |
| 5,268,461 | A | 12/1993 | Shoji et al. |
| 5,308,531 | A | 5/1994 | Uffer et al. |
| 5,317,010 | A | 5/1994 | Pang et al. |
| 5,369,095 | A | 11/1994 | Kee et al. |
| 5,457,100 | A | 10/1995 | Daniel |
| 5,550,220 | A | 8/1996 | Meyer et al. |
| 5,556,757 | A | 9/1996 | Alstyne et al. |
| 5,556,940 | A | 9/1996 | Willick et al. |

(Continued)

FOREIGN PATENT DOCUMENTS

| | | | |
|---|---|---|---|
| CN | 1303674 | A | 7/2001 |
| EP | 0396777 | A1 | 11/1990 |

(Continued)

OTHER PUBLICATIONS

US 5,849,884 A, 12/1998, Woiszwillo et al. (withdrawn)

Nunley, S., et al. Epilepsy & Behavior. 92, (2019), 53-56. (Year: 2019).*

Valtoco® FDA Label. FDA. (Year: 2020).*

"How does the nose work? The nasal mucosa," https://www.fitonasal2act.com/how-does-the-nose-work/the-nasal-mucosa/ (Accessed Nov. 5, 2019) [filed as EX2021 in IPR2019-00451].

"Intranasal Technology, Inc. Licenses Aegis Therapeutics' Intravail Drug Delivery Technology" (Business Wire) (Apr. 13, 2005) [filed as EX2028 in IPR2019-00451].

"Managing Epilepsy Well Network and Selected Self-Management Programs; Putting Collective Wisdom to Work for People with Epilepsy," Prevention Research Centers (PRC), CDC (Nov. 2016) [filed as EX2004 in IPR2019-00451, IPR2019-00450, IPR2019-00449].

(Continued)

*Primary Examiner* — Scarlett Y Goon
*Assistant Examiner* — Samuel L Galster
(74) *Attorney, Agent, or Firm* — DLA Piper LLP

(57) ABSTRACT

Compositions for intranasal delivery of benzodiazepines, such as diazepam, midazolam, and lorazepam and methods for their use to treat and prevent seizures in pediatric subjects aged 2-5, inclusive. Compositions for rapid therapeutic onset with a decreased incidence and/or severity of adverse effects after administration and methods of improving patient compliance with a prescribed treatment regimen.

33 Claims, No Drawings

(56) References Cited

U.S. PATENT DOCUMENTS

| | | | |
|---|---|---|---|
| 5,560,932 | A | 10/1996 | Bagchi et al. |
| 5,639,733 | A | 6/1997 | Koike et al. |
| 5,661,130 | A | 8/1997 | Meezan |
| 5,662,883 | A | 9/1997 | Bagchi et al. |
| 5,665,331 | A | 9/1997 | Bagchi et al. |
| 5,716,642 | A | 2/1998 | Bagchi et al. |
| 5,738,845 | A | 4/1998 | Imakawa |
| 5,780,062 | A | 7/1998 | Frank et al. |
| 5,789,375 | A | 8/1998 | Mukae et al. |
| 5,795,896 | A | 8/1998 | Lofroth et al. |
| 5,814,607 | A | 9/1998 | Patton |
| 5,817,634 | A | 10/1998 | Meezan et al. |
| 5,831,089 | A | 11/1998 | Huber |
| 5,861,510 | A | 1/1999 | Piscipio et al. |
| 5,863,949 | A | 1/1999 | Robinson et al. |
| 5,955,425 | A | 9/1999 | Morley et al. |
| 5,981,719 | A | 11/1999 | Woiszwillo et al. |
| 6,004,574 | A | 12/1999 | Backstrom et al. |
| 6,090,925 | A | 7/2000 | Woiszwillo et al. |
| 6,143,211 | A | 11/2000 | Mathiowitz et al. |
| 6,165,484 | A | 12/2000 | Read et al. |
| 6,193,985 | B1 | 2/2001 | Sonne |
| 6,235,224 | B1 | 5/2001 | Mathiowitz et al. |
| 6,254,854 | B1 | 7/2001 | Edwards et al. |
| 6,268,053 | B1 | 7/2001 | Woiszwillo et al. |
| 6,316,029 | B1 | 11/2001 | Jain et al. |
| 6,316,410 | B1 | 11/2001 | Barbier et al. |
| 6,375,986 | B1 | 4/2002 | Ryde et al. |
| 6,395,300 | B1 | 5/2002 | Straub et al. |
| 6,428,814 | B1 | 8/2002 | Bosch |
| 6,458,387 | B1 | 10/2002 | Scott et al. |
| 6,461,591 | B1 | 10/2002 | Keller et al. |
| 6,482,516 | B1 | 11/2002 | Sadek et al. |
| 6,482,834 | B2 | 11/2002 | Spada et al. |
| 6,495,498 | B2 | 12/2002 | Niemiec et al. |
| 6,524,557 | B1 | 2/2003 | Backstrom et al. |
| 6,551,578 | B2 | 4/2003 | Adjei et al. |
| 6,607,784 | B2 | 8/2003 | Kipp et al. |
| 6,608,073 | B1 | 8/2003 | Hussain et al. |
| 6,610,271 | B2 | 8/2003 | Wermeling |
| 6,616,914 | B2 | 9/2003 | Ward et al. |
| 6,627,211 | B1 | 9/2003 | Choi et al. |
| 6,794,357 | B1 | 9/2004 | Backstrom et al. |
| 6,855,332 | B2 | 2/2005 | Gizurarson et al. |
| 6,869,617 | B2 | 3/2005 | Kipp |
| 6,884,436 | B2 | 4/2005 | Kipp |
| 6,908,626 | B2 | 6/2005 | Cooper et al. |
| 6,932,962 | B1 | 8/2005 | Backstrom et al. |
| 6,991,785 | B2 | 1/2006 | Frey, II |
| 7,008,920 | B2 | 3/2006 | Kimura et al. |
| 7,037,528 | B2 | 5/2006 | Kipp |
| 7,132,112 | B2 | 11/2006 | Choi et al. |
| 7,220,402 | B1 | 5/2007 | Andersen et al. |
| 7,425,542 | B2 | 9/2008 | Maggio |
| 7,434,579 | B2 | 10/2008 | Young et al. |
| 7,524,510 | B2 | 4/2009 | Arnold et al. |
| 8,530,463 | B2 | 9/2013 | Cartt et al. |
| 8,895,546 | B2 | 11/2014 | Cartt et al. |
| 8,927,497 | B2 | 1/2015 | Maggio |
| 9,192,570 | B2 | 11/2015 | Wyse et al. |
| 9,642,913 | B2 | 5/2017 | Maggio |
| 9,763,876 | B2 | 9/2017 | Cartt et al. |
| 10,265,402 | B2 | 4/2019 | Maggio |
| 12,268,664 | B1 | 4/2025 | Cartt et al. |
| 12,324,852 | B2 | 6/2025 | Cartt et al. |
| 12,337,061 | B2 | 6/2025 | Cartt et al. |
| 12,521,400 | B2 | 1/2026 | Cartt et al. |
| 2001/0042932 | A1 | 11/2001 | Mathiowitz et al. |
| 2002/0110524 | A1 | 8/2002 | Cowan et al. |
| 2002/0127278 | A1 | 9/2002 | Kipp |
| 2002/0141971 | A1 | 10/2002 | Frey, II |
| 2002/0168402 | A1 | 11/2002 | Kipp |
| 2003/0017203 | A1 | 1/2003 | Crotts et al. |
| 2003/0031719 | A1 | 2/2003 | Kipp et al. |
| 2003/0040497 | A1 | 2/2003 | Teng et al. |
| 2003/0087820 | A1 | 5/2003 | Young et al. |
| 2003/0095928 | A1 | 5/2003 | McGurk et al. |
| 2003/0100755 | A1 | 5/2003 | Sham et al. |
| 2003/0118547 | A1 | 6/2003 | Vandenberg |
| 2003/0118594 | A1 | 6/2003 | Nag et al. |
| 2003/0158206 | A1 | 8/2003 | Billotte et al. |
| 2003/0170206 | A1 | 9/2003 | Rasmussen et al. |
| 2003/0170752 | A1 | 9/2003 | Andersen et al. |
| 2003/0181411 | A1 | 9/2003 | Bosch et al. |
| 2004/0101482 | A1 | 5/2004 | Sanders |
| 2004/0115135 | A1 | 6/2004 | Quay |
| 2004/0126358 | A1 | 7/2004 | Warne et al. |
| 2004/0141923 | A1 | 7/2004 | Dugger, III et al. |
| 2004/0147473 | A1 | 7/2004 | Wardell, Jr. |
| 2004/0176359 | A1 | 9/2004 | Wermeling |
| 2004/0209814 | A1 | 10/2004 | Nauck et al. |
| 2004/0248846 | A1 | 12/2004 | Quay et al. |
| 2004/0258663 | A1 | 12/2004 | Quay et al. |
| 2005/0130260 | A1 | 6/2005 | Linden et al. |
| 2005/0153956 | A1 | 7/2005 | Merkus |
| 2005/0215475 | A1 | 9/2005 | Ong et al. |
| 2005/0234101 | A1 | 10/2005 | Stenkamp et al. |
| 2005/0276843 | A1 | 12/2005 | Quay et al. |
| 2006/0045868 | A1 | 3/2006 | Meezan et al. |
| 2006/0045869 | A1 | 3/2006 | Meezan et al. |
| 2006/0046962 | A1 | 3/2006 | Meezan et al. |
| 2006/0046969 | A1 | 3/2006 | Maggio |
| 2006/0074025 | A1 | 4/2006 | Quay et al. |
| 2006/0106227 | A1 | 5/2006 | Reddy et al. |
| 2006/0147386 | A1 | 7/2006 | Wermeling |
| 2006/0178290 | A1 | 8/2006 | Bara |
| 2006/0183674 | A1 | 8/2006 | Brand et al. |
| 2006/0198896 | A1 | 9/2006 | Liversidge et al. |
| 2006/0222597 | A1 | 10/2006 | Dugger |
| 2007/0059254 | A1 | 3/2007 | Maggio |
| 2007/0098805 | A1 | 5/2007 | Liversidge |
| 2007/0111938 | A1 | 5/2007 | Pert et al. |
| 2007/0298010 | A1 | 12/2007 | Maggio |
| 2008/0070904 | A1 | 3/2008 | Jamieson et al. |
| 2008/0076761 | A1 | 3/2008 | Jamieson et al. |
| 2008/0192461 | A1 | 8/2008 | Maggio |
| 2008/0200418 | A1 | 8/2008 | Maggio |
| 2008/0248123 | A1 | 10/2008 | Swanson et al. |
| 2008/0268032 | A1 | 10/2008 | Maggio |
| 2008/0275030 | A1 | 11/2008 | Gizurarson et al. |
| 2008/0279784 | A1 | 11/2008 | Cartt |
| 2008/0299079 | A1 | 12/2008 | Meezan et al. |
| 2009/0004281 | A1 | 1/2009 | Nghiem et al. |
| 2009/0047234 | A1 | 2/2009 | Touitou et al. |
| 2009/0047347 | A1 | 2/2009 | Maggio |
| 2009/0130216 | A1 | 5/2009 | Cartt et al. |
| 2009/0156478 | A1 | 6/2009 | Lau et al. |
| 2009/0163447 | A1 | 6/2009 | Maggio |
| 2009/0258865 | A1 | 10/2009 | Cartt et al. |
| 2009/0297619 | A1 | 12/2009 | Swanson et al. |
| 2009/0304801 | A1 | 12/2009 | Liversidge et al. |
| 2009/0326193 | A1 | 12/2009 | Maggio et al. |
| 2010/0034880 | A1 | 2/2010 | Sintov et al. |
| 2010/0068209 | A1 | 3/2010 | Maggio |
| 2010/0112050 | A1 | 5/2010 | Ryoo et al. |
| 2010/0160378 | A1 | 6/2010 | Maggio |
| 2010/0203014 | A1 | 8/2010 | Maggio |
| 2010/0203119 | A1 | 8/2010 | Leane et al. |
| 2010/0209485 | A1 | 8/2010 | Maggio |
| 2011/0172211 | A1 | 7/2011 | Baek et al. |
| 2011/0257096 | A1 | 10/2011 | Maggio |
| 2012/0196941 | A1 | 8/2012 | Maggio |
| 2013/0065886 | A1 | 3/2013 | Cartt et al. |
| 2013/0224300 | A1 | 8/2013 | Maggio |
| 2013/0253009 | A1 | 9/2013 | Maggio |
| 2014/0128479 | A1 | 5/2014 | Maggio |
| 2014/0170220 | A1 | 6/2014 | Cartt et al. |
| 2015/0065491 | A1 | 3/2015 | Cartt et al. |
| 2016/0199296 | A1 | 7/2016 | Bergenhem et al. |
| 2017/0196884 | A1 | 7/2017 | Cartt et al. |
| 2020/0038320 | A1 | 2/2020 | Cartt et al. |
| 2021/0299089 | A1 | 9/2021 | Cartt et al. |
| 2022/0062227 | A1 | 3/2022 | Cartt et al. |
| 2022/0218598 | A1 | 7/2022 | Misra et al. |

(56) References Cited

U.S. PATENT DOCUMENTS

| | | | | |
|---|---|---|---|---|
| 2023/0104144 | A1* | 4/2023 | Cartt | A61P 25/22 514/183 |
| 2024/0299290 | A1* | 9/2024 | Carrazana | A61K 9/0043 |
| 2025/0281394 | A1 | 9/2025 | Cartt et al. | |

FOREIGN PATENT DOCUMENTS

| | | | |
|---|---|---|---|
| EP | 0606046 | A1 | 7/1994 |
| EP | 0780386 | A1 | 6/1997 |
| EP | 0818442 | A2 | 1/1998 |
| EP | 0931788 | A2 | 7/1999 |
| EP | 0945485 | A1 | 9/1999 |
| EP | 1004578 | A2 | 5/2000 |
| EP | 1208863 | A2 | 5/2002 |
| EP | 1417972 | A1 | 5/2004 |
| JP | S60208911 | A | 10/1985 |
| JP | S61267528 | A | 11/1986 |
| JP | H01151528 | A | 6/1989 |
| JP | H05507085 | A | 10/1993 |
| JP | 2003505403 | A | 2/2003 |
| JP | 2005508939 | A | 4/2005 |
| JP | 2007510722 | A | 4/2007 |
| JP | 2009515895 | A | 4/2009 |
| JP | 2011516425 | A | 5/2011 |
| JP | 6883918 | B2 | 5/2021 |
| WO | 1990005719 | A1 | 5/1990 |
| WO | 1991019481 | A1 | 12/1991 |
| WO | 1994005262 | A1 | 3/1994 |
| WO | 1995000151 | A1 | 1/1995 |
| WO | 1995031217 | A1 | 11/1995 |
| WO | 1996027583 | A1 | 9/1996 |
| WO | 1996033172 | A1 | 10/1996 |
| WO | 1997014407 | A1 | 4/1997 |
| WO | 1998003516 | A1 | 1/1998 |
| WO | 1998007697 | A1 | 2/1998 |
| WO | 1998030566 | A1 | 7/1998 |
| WO | 1998033768 | A1 | 8/1998 |
| WO | 1998034915 | A1 | 8/1998 |
| WO | 1998034918 | A1 | 8/1998 |
| WO | 1999007675 | A1 | 2/1999 |
| WO | 1999029667 | A1 | 6/1999 |
| WO | 1999052889 | A1 | 10/1999 |
| WO | 1999052910 | A1 | 10/1999 |
| WO | 2000001390 | A1 | 1/2000 |
| WO | 2000074681 | A1 | 12/2000 |
| WO | 2003004015 | A1 | 1/2003 |
| WO | 2003007978 | A1 | 1/2003 |
| WO | 2003055464 | A1 | 7/2003 |
| WO | 2005018565 | A2 | 3/2005 |
| WO | 2005044234 | A2 | 5/2005 |
| WO | 2005089768 | A1 | 9/2005 |
| WO | 2005117830 | A1 | 12/2005 |
| WO | 2006025882 | A2 | 3/2006 |
| WO | 2006051110 | A2 | 5/2006 |
| WO | 2006055603 | A2 | 5/2006 |
| WO | 2006075123 | A1 | 7/2006 |
| WO | 2006088894 | A2 | 8/2006 |
| WO | 2007043057 | A2 | 4/2007 |
| WO | 2007144081 | A2 | 12/2007 |
| WO | 2008027395 | A2 | 3/2008 |
| WO | 2008120207 | A2 | 10/2008 |
| WO | 2008137960 | A1 | 11/2008 |
| WO | 2009120933 | A2 | 10/2009 |
| WO | 2009121039 | A2 | 10/2009 |
| WO | 2012174158 | A2 | 12/2012 |
| WO | 2022150540 | A1 | 7/2022 |

OTHER PUBLICATIONS

"Neurelis Files New Drug Application With the FDA for VALTOCO (Diazepam Nasal Spray), An Investigational Treatment for Pediatric, Adolescent And Adult Epilepsy Patients," (2018) (Accessed Nov. 1, 2019) [filed as EX2023 in IPR2019-00451].

"Neurelis Receives FDA Orphan Drug Designation for NRL-1 in the Treatment of Acute Repetitive Seizures," https://www.neurelis.com/neurelis-news/fda-orphan-drug-designation (2015) (Accessed Nov. 1, 2019) [filed as EX2024 in IPR2019-00451].

"UCB announces NAYZILAM (midazolam) nasal spray now approved by FDA to treat intermittent, stereotypic episodes of frequent seizure activity in people living with epilepsy in the U.S.," UCB Press Release (2019) (Accessed Oct. 31, 2019) [filed as EX2018 in IPR2019-00451].

Affidavit of Robert Cleary executed Nov. 21, 2019 [filed as EX2025 in IPR2019-00451].

Affidavit of Ronald Figueroa executed Nov. 21, 2019 [filed as EX2026 in IPR2019-00451].

Ahmad S, Ellis J, Kamwendo H et al. Efficacy and safety of intranasal lorazepam versus intramuscular paraldehyde for protracted convulsions in children: an open label trial. Lancet 2006; 367: 1591-1597 [filed as EX1144 in IPR2019-00451].

Ahsan et al. "Effects of the permeability enhancers, tetradecylmaltoside and dimethyl-.beta.-cyclodextrin, on insulin movement across human bronchial epithelial cells (16HBE140-)" 2003, European Journal of Pharmaceutical. Sciences 20:27-34.

Ahsan et al. "Sucrose cocoate, a component of cosmetic preparations, enhances nasal and ocular peptide absorption" 2003; Int J Pharm 251:195-203.

Albert et al. "Pharmacokinetics of diphenhydramine in man" 1975, J. Pharmacokinet. Biopharm., 3(3):159-170.

Appellant Neurelis Inc.'s Opening Brief filed Feb. 2, 2021 in Appeal Case No. 21-1038 (Court of Appeals for the Federal Circuit).

Appellant Neurelis Inc.'s Reply Brief filed May 3, 2021 in Appeal Case No. 21-1038 (Court of Appeals for the Federal Circuit).

Arnold et al. "Correlation of tetradecylmaltoside induced increases in nasal peptide drug delivery with morphological changes in nasal eithelial cells" 2004, J. Pharm. Sci. 93(9):2205-2213.

Assignment of U.S. Appl. No. 12/116,842 recorded at Reel:Frame 027955:0600 on Mar. 29, 2012 [filed as EX1049 in IPR2019-00451].

Assignment of U.S. Appl. No. 12/933,701 recorded at Reel:Frame 025034:0531 on Sep. 23, 2010 [filed as EX1047 in IPR2019-00451, IPR2019-00450, IPR2019-00449].

Australian First Examination Report for AU 2009228093 dated Jul. 19, 2013.

Beam et al. "Blood, Brain, Cerebrospinal Fluid Concentrations of Several Antobiotics in Rabbits with Intact and Inflamed Meninges" Dec. 1977, Antimicrobal Agents and Chemotherapy, pp. 710-716.

Bechgaard E. et al., "Solubilization of Various Benzodiazepines for Intranasal Administration, A Pilot Study," Pharmaceutical Development and Technology 2: 293-296 (1997) [filed as EX2007 in IPR2019-00451].

Behl et al., Effects of physicochemical properties and other factors on systemic nasal drug delivery. Advanced Drug Delivery Reviews 29 (1998) 89: 116 [filed as EX1039 in IPR2019-00451, IPR2019-00450, IPR2019-00449].

Berrocoso et al. "Opiates as Anti-depressents" 2009, Current Pharma Design 15:1612-1622.

Bhairi "A guide to the properties and uses of detergents in biological systems" 2001, Calbiochem, pp. 1-42.

Bhattacharyya M, Kalra V, Gulati S. Intranasal midazolam vs rectal diazepam in acute childhood seizures. Pediatric Neurology 2006; 34: 355-359 [filed as EX1140 in IPR2019-00451].

Birkett et al. "Bioavailability and First Pass Clearance" 1991, Australian Prescriber 14:4-16.

Birkett et al. "How Drugs are Cleared by the Liver" 1990; Australian Prescriber, 13(4):88-89.

Brown et al. "Affinity Purification of a Somatostatin Receptor-G-Protein Complex Demonstrates Specificity in Receptor-G-Protein Coupling" 1993, J. Biol. Chem. 268.9:6668-6676.

Budavari, et al, Editors, The Merck Index, 12th Edition (1996), p. xiii-xiv, xv-xviii, 508, 189, 641-642, 1712 [filed as EX1076 in IPR2019-00451].

Burstein AH, Modica R, Hatton M et al. Pharmacokinetics and pharmacodynamics of midazolam after intranasal administration. J Clin Pharmacol 1997; 37: 711-718 [filed as EX1129 in IPR2019-00451].

(56) References Cited

OTHER PUBLICATIONS

Canadian Office Action for CA 2723470 dated Jun. 7, 2012.
Canadian Office Action for CA 2756690 dated Feb. 19, 2015.
Canadian Office Action for CA 2756690 dated Oct. 20, 2015.
Castro et al. "Ecologically safe alkyl glucoside-based gemini surfactants" 2005, ARKIVOC, xii:253-267.
CDER Sep. 19, 2019—Abbreviated Approval Products: 505(b)(2) or ANDA at https://www.fda.gov/drugs/cder-small-business-industry-assistance-sbia/abbreviated-approval-pathways-drug-product-505b2-or-and-September-19-2019-issue (2019) [filed as EX1147 in IPR2019-00451].
Chavanpatil et al. "Nasal drug delivery of sumatriptan succinate" May 2005, Pharmazie. 60(5):347-349.
Chen et al. "Peptide Drug Permeation Enhancement by Select Classes of Lipids" Dec. 10-14, 2005, presented at the 45th American Society of Cell Biology, S.F., CA, 1 page.
Chen-Quay et al. "Identification of tight junction modulating lipids" 2009, J, Pharm. Sci., 98(2):606-619.
Chien, Y.W et al., "Nasal Systemic Drug Delivery", Chapter 1, Anatomy and Physiology of the Nose, Drugs and the Pharmaceutical Sciences, vol. 39, Marcel Decker, 1989 [filed as EX1082 in IPR2019-00451].
Chinese Office Action for CN 201280039077.9 dated Dec. 26, 2014.
Chinese Office Action for CN 201280039077.9 dated Nov. 21, 2016.
Chinese Office Action for CN 201710940124.1 dated Sep. 28, 2020.
Chinese Office Action for CN 201710940124.1 dated Nov. 25, 2019.
Chinese Office Action for CN 200980157305.0 dated Jan. 28, 2013.
Chinese Reexamination Report for CN 201280039077.9 dated Jun. 29, 2017.
Chinese Office Action for CN 201280039077.9 dated Aug. 11, 2015.
Chinese Office Action for CN 201280039077.9 dated Mar. 17, 2016.
Chiou et al. "Improvement of Systemic Absorption of Insulin Through Eyes with Absorption Enhancers" Oct. 1989, Journal of Pharmaceutical Sciences, 78(10):815-818.
Chiou et al. "Systemic delivery of Insulin Through Eyes to lower the glucose concentration" 1989, Journal of Ocular Pharmacology 5(1):81-91.
Christensen et al. "Once-Weekly GLP-1 Agonists: How do they differ from exenatide and liraglutide?" 2010, Curr. Diab. Rep. 10(2):124-132.
Cole C. et al., "Community Survey of Carer's: Individual Epilepsy Guidelines (IEG) for Rescue Medication," Seizure 18: 220-224 (2009) [filed as EX2015 in IPR2019-00451].
Murakami et al. "Assessment of Enhancing Ability of Medium-Chain Alkyl Saccharides as New Absorption Enhancers in Rat Rectum," Feb. 1992, International Journal of Pharmaceutics 79(1-3):159-169.
Mygind N., "Nasal Allergy," 9 (Blackwell Scientific Publications, 1979) [filed as EX2022 in IPR2019-00451].
Nayzilam Product Label and Instructions for Use Revised May 2019 [filed as EX1072 in IPR2019-00451].
Newman "Aerosol Deposition Considerations in Inhalation Therapy" 1985, Chest 152S-160S.
Notice Forwarding Certified List filed Nov. 18, 2020 in Appeal Case No. 21-1038 (Court of Appeals for the Federal Circuit).
Notification of Receipt of Precedential Opinion Panel (POP) Request filed Oct. 2, 2019 in IPR2019-00451.
O'Dell et al., School nurses' experience with administration of rectal diazepam gel for seizures. J Sch Nurs., 23(3) (Jun. 2007): 166-169 [filed as EX1029 in IPR2019-00451, IPR2019-00450, IPR2019-00449].
O'Donnell et al. "Therapeutic Potential of a Long Acting Somatostatin Analogue in Gastrointestinal Diseases" 1989, Gut 30.9:1165-1172.
O'Regan M, Brown J, Clarke M., Nasal rather than rectal benzodiazepines in the management of acute childhood seizures. Develop Med and Child Neurol 1996; 38: 1037-1045 [filed as EX1136 in IPR2019-00451].
Ogiso et al. "Percutaneous Absorption of Elcatonin Chemical and Hypocalcemic Effect in Rat" Feb. 1991, The Pharmaceutical Society of Japan, Tokyo, Japan—Chemical & Pharmaceutical Bulletin 39(2):449-453.
Olesen et al. "The Headaches" 2005, Lippincott Williams & Wilkins, p. 474.
Order Denying POP Request filed Nov. 15, 2019 in IPR2019-00451.
Osborne et al., Skin Penetration Enhancers Cited in the Technical Literature, Pharmaceutical Technology (Nov. 1997) [filed as EX1024 in IPR2019-00451, IPR2019-00450, IPR2019-00449].
Pang T, Hirsch L. Treatment of convulsive and nonconvulsive status epilepticus. Cur Treat Options Neurol 2005; 7: 247-259 [filed as EX1107 in IPR2019-00451].
Parties' Joint Submission of Patent Owner's Identification of New Arguments and Petitioner's Responses Thereto filed Feb. 25, 2020 in IPR2019-00451.
Patent Owner's Notice of Appeal filed Oct. 8, 2020 in IPR2019-00451.
Patent Owner's Preliminary Response filed May 21, 2019 in IPR2019-00451.
Patent Owner's Preliminary Response filed May 6, 2019 in IPR2019-00449.
Patent Owner's Preliminary Response filed May 6, 2019 in IPR2019-00450.
Patent Owner's Request for Rehearing filed Aug. 27, 2019 in IPR2019-00451.
Patent Owner's Response to the Petition filed Nov. 5, 2019 in IPR2019-00451.
Patent Owner's Surreply to Patent Owner's Response filed Mar. 10, 2020 in IPR2019-00451.
Paulsson et al. "Controlled drug release from gels using surfactant aggregates. II. Vesicles formed from mixtures of amphiphilic drugs and oppositely charged surfactants" 2001, Pharm. Res. 18(11):1586-1592.
PDR 54th Edition 2000, DIASTAT (diazepam rectal gel); MIACALCIN (Calcitonin Nasal Spray); VALIUM (diazepam injection), Physicians' Desk Reference [filed as EX1042 in IPR2019-00451, IPR2019-00450, IPR2019-00449].
Petition for Inter Partes Review of U.S. Pat. No. 9,736,876 filed Jan. 28, 2019 in IPR2019-00449.
Petition for Inter Partes Review of U.S. Pat. No. 9,736,876 filed Jan. 29, 2019 in IPR2019-00450.
Petition for Inter Partes Review of U.S. Pat. No. 9,736,876 filed Jan. 29, 2019 in IPR2019-00451.
Petitioner's Reply to Patent Owner's Response to the Petition filed Jan. 28, 2020 in IPR2019-00451.
Petitioner's Request for Rehearing Pursuant to 37 C.F.R. 42.71(d) filed Sep. 3, 2019 in IPR2019-00449.
Phillips "The challenge of gene therapy and DNA delivery" 2001; J Pharm Pharmacology 53:1169-1174.
Pillion et al. "Synthetic long-chain alkyl maltosides and alkyl sucrose esters as enhancers of nasal insulin absorption" 2002, J. Pharm. Sci. 91:1456-1462.
Pillion et al."Systemic Absorption of Insulin Delivered Topically to the Rat Eye", Nov. 1991, Investigative Ophthalmology & Visual Science 32(12):3021-3027.
Pirollo et al. "Targeted delivery of small interfering RNA: approaching effective cancer therapies", 2008, Cancer Res. 68(5):1247-1250.
Prasad K, Krishman P, Al-Roomi K et al., Anticonvulsant therapy for status epilepticus. Br J Clin Pharmacol 2007; 63: 640-647 [filed as EX1112 in IPR2019-00451].
Record of Oral Hearing held May 14, 2020 filed May 27, 2020 in IPR2019-00451.
Richards "Inactivation of resistant Pseudomonas aeruginosa by antibacterial combinations", 1971, J. Pharm. Pharmacol. 23:136S-140S.
Riss J. et al., "Benzodiazepines in Epilepsy: Pharmacology and Pharmacokinetics," Acta Neurologica Scandinavica 118: 69-86 (2008) [filed as EX2013 in IPR2019-00451].
Ritschel, Handbook of Basic Pharmacokinetics, Chapter 36 (Bioavailability and Bioequivalence). Drug Intelligence Publications, Illinois (1992) [filed as EX1023 in IPR2019-00451, IPR2019-00450, IPR2019-00449].

(56) References Cited

OTHER PUBLICATIONS

Rowe et al., editors, Handbook of Pharmaceutical Excipients, Fourth Edition (2003), Monographs, American Pharmaceutical Association, Washington DC (2003), pp. 13-15, 27-29, 53-55, 257-259, 414-416, 454-459, 521-523, 535-537, 659-660 [filed as EX1031 in IPR2019-00451, IPR2019-00450, IPR2019-00449].
Rudy AC, Coda BA, Archer SM, Wermeling DP. A multiple dose phase 1 study of intranasal hydromorphone hydrochloride in healthy volunteers. Anesth Analg 2004; 99:1379-1386 [filed as EX1122 in IPR2019-00451].
Rule 36 Judgment entered Oct. 7, 2021, U.S. Court of Appeals for the Federal Circuit, *Neurelis, Inc.*, Appellant v. *Aquestive Therapeutics, Inc.*, Appellee, Appeal No. 2021-1038, affirming decision in IPR2019-00451 (U.S. Pat. No. 9,763,876).
Salem et al. "Approaches to the Pharmacological Treatment of Obesity" Feb. 5, 2010, Expert Rev. of Clinical Pharmacology 3.1:73-88, accessed online form http://www.medscape.com.
Salzman et al. "Intranasal Aerosolized Insulin" Apr. 25, 1985, The New England Journal of Medicine 312 (17):1078-1084.
Sanders et al. "Pharmacokinetics of ergotamine in healthy volunteers following oral and rectal dosing" 1986, Eur. J. Clin. Pharmacol. 30(3):331-334.
Schmidt et al. "New Methods for the Synthesis of Glycosides and Oligosaccharides: Are There Alternatives to the Koenigs-Knorr Method?" 1986, Angew. Chem. Int. Ed. Engl. 25:212-235 (abstract only).
Schols-Hendriks M. et al., "Absorption of Clonazepam After Intranasal and Buccal Administration," British Journal of Clinical Pharmacology 39: 449-451 (1995) [filed as EX2010 in IPR2019-00451].
Schols-Hendriks MWG, Lohman JJHM, Janknegt R et al. Absorption of clonazepam after intranasal and buccal administration. Br J Clin Pharmacol, 1995; 39: 449-451 [filed as EX1131 in IPR2019-00451].
Senel et al. "Drug permeation enhancement via buccal route: possibilities and limitations" 2001, J. Controlled Release 72:133-144.
Shim et al. "Administration Route Dependent Bioavailability of Interferon-.alpha. and Effect of Bile Salts on the Nasal Absorption" 1993, Drug Development and Industrial Pharmacy 19(10):1183-1199.
SIGMA Chemical Company Catalog (1988) [filed as EX2006 in IPR2019-00451].
U.S. Appl. No. 17/228,514, filed Apr. 12, 2021.
U.S. Appl. No. 17/332,800, filed May 27, 2021.
U.S. Office Action for U.S. Appl. No. 15/955,397 dated Oct. 7, 2019.
U.S. Appl. No. 61/040,558, filed Mar. 28, 2008 [filed as EX1008 in IPR2019-00451, IPR2019-00450, IPR2019-00449].
U.S. Appl. No. 61/497,017, filed Jun. 14, 2011 [filed as EX1005 in IPR2019-00451, IPR2019-00450, IPR2019-00449].
U.S. Appl. No. 61/570,110, filed Dec. 13, 2011 [filed as EX1006 in IPR2019-00451, IPR2019-00450, IPR2019-00449].
USP NF 2003, The United States Pharmacopeia, The National Formulary, United States Pharmacopeial Convention, Inc., (1088) In Vitro and In Vivo Evaluation, p. 2334-2339 [filed as EX1044 in IPR2019-00451, IPR2019-00450, IPR2019-00449].
USP/NF 2003, The Official Compendia of Standards, Ethanol, 2002, Alcohol, p. 59-60 [filed as EX1078 in IPR2019-00451].
VALIUM Tablet Label, Roche, Jan. 2008 [filed as EX1080 in IPR2019-00451].
Van Der Lubben et al. "Chitosan and its derivatives in mucosal drug and vaccine delivery" 2001, Eur. J. Pharm. Sci. 14(3):201-207.
Vidal et al. "Making sense of antisense" 2005, European Journal of Cancer 41:2812-2818.
Wang "Drug Delivery and Release System" Aug. 2007, China Medical Science and Technology Press, pp. 356-357.
Wang HC, Chang WN, Chang HW et al. Factors predictive of outcome in posttraumatic seizures. J Trauma 2008; 64: 883-888 [filed as EX1103 in IPR2019-00451].
Watanabe et al. "Antibacterial Carbohydrate Monoesters Suppressing Cell Growth of *Streptococcus* Mutans in the Presence of Sucrose," Sep. 2000, Current Microbiology 41(3):210-213 (abstract only).
Weber et al. "Metabolism of orally administered alkyl beta-glycosides in the mouse"; 1984, J. Nutr., 114:247-254.
Webpage for Anatrace products of Affymetrix, http://www.affymetrix.com/estore/browse/level.sub.--three.sub.--category.-sub.-and.sub.--products.jsp?category=35843&categoryIdClicked=35843&expand- =true&parent=35900, accessed online on Dec. 13, 2012.
Weidinger-Hendeles et al. "Oral Phenylephrine: an ineffective replacement for pseudoephedrine?" 2006, J. Allergy Clin. Immunol. 118. 1:279-280.
Wermeling DP, Miller JL, Archer SM et al. Bioavailability and pharmacokinetics of lorazepam after intranasal, intravenous, and intramuscular administration. J Clin Pharmacol, 2001; 41: 1225-1231 [filed as EX1134 in IPR2019-00451].
Wermeling et al. "Pharmacokinetics and pharmacodynamics of a new intranasal midazolam formulation in healthy volunteers" 2006, Anesthesia & Analgesia 103 (2):344-349.
Wermeling, D.P., Intranasal delivery of antiepileptic medications for treatment of seizures, Neurotherapeutics, Apr. 2009, 6(2):352-358 [filed as EX1151 in IPR2019-00451].
Wilson, M.T., S. Macleod, and M.E. O'Regan, Nasal/buccal midazolam use in the community. Arch Dis Child, 2004. 89(1):50-51 [filed as EX1141 in IPR2019-00451].
Wolfe T, Bernstone T, Intranasal Drug Delivery: An Alternative to Intravenous Administration in Selected Emergency Cases, J Emerg Nurs. Apr. 2004;30(2): 141-147 [filed as EX1145 in IPR2019-00451].
Wolfe T, Macfarlane T. Intranasal midazolam therapy for pediatric status epilepticus. Am J Emerg Med 2006; 24: 343-346 [filed as EX1110 in IPR2019-00451].
Xinlei et al."Triptan. Medicament and Migraine", 2001, World Pharmacy (Synthetic Drug and Biochemical Drug Formulation Fascicule), 22(2):91-92.
Yamamoto et al. "The Ocular Route for Systemic Insulin Delivery in the Albino Rabbit" 1989, J. Pharmacology and Exper. Thera. 249.1:249-255.
International Search Report and Written Opinion for PCT/US2022/011538 dated Mar. 30, 2022.
Hogan et al. "Pharmacokinetics and safety of VALTOCO (NRL-1; diazepam nasal spray) in patients with epilepsy during seizure (ictal/peri-ictal) and nonseizure (interictal) conditions: a phase 1, open-label study" Apr. 27, 2020, Epilepsia 61(5);935-943.
Wikipedia "Benzodiazepine overdose" Sep. 23, 2019, retrieved on Mar. 10, 2022 from https://en.wikipedia.org/w/index.php?title+Benzodiazepine_overdose&oldid=917464003 entire document.
Worrell et al. "Focal ictal beta discharge on scalp EEG predicts excellent outcome of frontal lobe epilepsy surgery" Mar. 2002, Epilepsia 43(3):277-282.
Wermeling, D, Record K, Kelly T et al., Pharmacokinetics and pharmacodynamics of a new intranasal midazolam formulation in healthy volunteers. Anesth Analg 2006; 103: 344-349 [filed as EX1130 in IPR2019-00451].
U.S. Petition for Inter Partes Review 2019-00449 for U.S. Pat. No. 9,763,876 filed Jan. 28, 2019.
U.S. Petition for Inter Partes Review 2019-00450 for U.S. Pat. No. 9,763,876 filed Jan. 29, 2019.
U.S. Petition for Inter Partes Review 2019-00451 for U.S. Pat. No. 9,763,876 filed Jan. 29, 2019.
U.S. Appl. No. 17/336,389, filed Jun. 2, 2021.
International Search Report and Written Opinion for PCT/US2022/032951 dated Aug. 24, 2022.
Colombo, Mucosal Drug Delivery, Nasal. Encyclopedia of Controlled Drug Delivery (Mathiowitz, editor), John Wiley & Sons, vol. 2 (1999): 592-605 [filed as EX1037 in IPR2019-00451, IPR2019-00450, IPR2019-00449].
Constantino HR, Illum L, Brandt G et al., Intranasal delivery: Physicochemical and therapeutic aspects, Intl J Pharmaceutics 2007; 337: 1-24 [filed as EX1118 in IPR2019-00451].

(56) References Cited

OTHER PUBLICATIONS

Corbo G. et al., "Measurement of Nasal Mucociliary Clearance," Archives of Disease in Childhood 64: 546-550 (1989) [filed as EX2020 in IPR2019-00451].
Corrected Brief for Appellee Aquestive Therapeutics, Inc. filed Mar. 31, 2021 in Appeal Case No. 21-1038 (Court of Appeals for the Federal Circuit).
Dale O., Nilsen T., Loftsson T. Intranasal midazolam: a comparison of two delivery devices in human volunteers. J Pharmacy Pharmacol 2006; 58:1311-1318 [filed as EX1128 in IPR2019-00451].
Daniel P. Wermeling Deposition Transcript, Feb. 26, 2020 [filed as EX2031 in IPR2019-00451].
Davis et al. "Absorption enhancers for nasal drug delivery" 2003, Clin. Pharmacokine. 42(13):1107-1128.
Davis GA, Rudy AC, Archer SA, Wermeling DP, McNamara PJ. Effect of fluticasone propionate nasal spray on bioavailability of hydromorphone hydrochloride in patients with allergic rhinitis. Pharmacotherapy 2004; 24: 26-32 [filed as EX1119 in IPR2019-00451].
Davis GA, Rudy AC, Archer SM, Wermeling DP, McNamara PJ., Bioavailability and pharmacokinetics of intranasal hydromorphone in patients experiencing vasomotor rhinitis. Clin Drug Invest 2004; 24: 1-7 [filed as EX1120 in IPR2019-00451].
Davis, Delivery of peptide and non-peptide drugs through the respiratory tract. Pharmaceutical Science & Technology Today, 2(11) (Nov. 1999): 450-456 [filed as EX1035 in IPR2019-00451, IPR2019-00450, IPR2019-00449].
De Vry et al. "Effects of selected serotonin 5-HT(1) and 5-HT(2) receptor agonists on feeding behavior: possible mechanisms of action" 2000, Neurosci. Biobehav. Rev. 24(3):341-353.
Decision Denying Institution of Inter Partes Review of U.S. Pat. No. 9,736,876 filed Aug. 1, 2019 in IPR2019-00449.
Decision Denying Institution of Inter Partes Review of U.S. Pat. No. 9,736,876 filed Aug. 1, 2019 in IPR2019-00450.
Decision Denying Patent Owner's Request on Rehearing of Decision on Institution filed Sep. 27, 2019 in IPR2019-00451.
Decision Denying Petitioner's Request for Rehearing of Decision Denying Institution of Inter Partes Review filed Sep. 27, 2019 in IPR2019-00449.
Decision Instituting Inter Partes Review of U.S. Pat. No. 9,736,876 filed Aug. 13, 2019 in IPR2019-00451.
Declaration of Daniel P. Wermeling, Pharm.D. executed Jan. 27, 2020 [filed as EX1150 in IPR2019-00451].
Declaration of Dr. Nicholas A. Peppas executed Dec. 6, 2018 [filed as EX1041 in IPR2019-00451].
Declaration of Dr. Nicholas A. Peppas executed Dec. 6, 2018 [filed as EX1041 in IPR2019-00449].
Declaration of Dr. Nicholas A. Peppas executed Dec. 6, 2018 [filed as EX1041 in IPR2019-00450].
Declaration of Dr. Sveinbjorn Gizurarson, Ph.D. executed Nov. 4, 2019 [filed as EX2012 in IPR2019-00451].
Declaration of Michael I. Chakansky executed Feb. 19, 2020 [filed as EX1152 in IPR2019-00451].
Definition of "encephalin" downloaded Sep. 13, 2012 at the medical-dictionary.thefreedictionary.com/p/encephalin.
Definition of "pilus" downloaded May 28, 2013, Merriam-Webster Medical Dictionary, http://www.merriam-webster.com/medical/pilus.
Definition of "villus", downloaded May 28, 2013, Merriam-Webster Medical Dictionary, http://www.merriam-webster.com/medical/villus.
Deshmukh et al., Lorazepam in the Treatment of Refractory Neonatal Seizures. Am J Dis Child., 140(10) (1986): 1042-1044 [filed as EX1036 in IPR2019-00451, IPR2019-00450, IPR2019-00449].
DIASTAT Label (2005) [filed as EX2017 in IPR2019-00451].
Dr. Nicholas Peppas Deposition Transcript, Oct. 24, 2019 [filed as EX2011 in IPR2019-00451].
Drewe et al. "Enteral absorption of octreotide: absorption enhancement by polyoxyethylene-24-cholesterol ether" 1993, Br. J. Pharmacol. 108(2):298-303.
Drug Prices from Internet (Accessed Jan. 24, 2020) [filed as EX1081 in IPR2019-00451].
Duquesnoy et al. "Comparative clinical pharmacokinetics of single doses of sumatriptan following subcutaneous, oral, rectal and intranasal administration" 1998, Eur. J. Pharm. Sci., 6(2):99-104.
Edman et al., (D) Routes of Delivery: Case Studies—(1) Nasal delivery of peptide drugs, Advanced Drug Delivery Reviews, 8 (1992): 165-177 [filed as EX1034 in IPR2019-00451, IPR2019-00450, IPR2019-00449].
Edman et al., Microspheres as a nasal delivery system for peptide drugs. Journal of Controlled Release, 21 (1992): 165-172 [filed as EX1032 in IPR2019-00451, IPR2019-00450, IPR2019-00449].
Eley et al. "In vitro assessment of alkylglycosides as permeability enhancers" 2001, AAPS PharmsciTech. 2(3):19:1-7.
Email sent Sep. 30, 2019 requesting Precedential Opinion Panel review [filed as EX3001 in IPR2019-00451].
Epilepsy Fast Facts, CDC (Center for Disease Control and Preventions), CDC 24/7: Saving Lives, Protection People, Apr. 9, 2019, pp. 1-2, available at https://www.cdc.gov/epilepsy/about/fast-facts.htm?CDC_ AA_refVal=https%3A%2F%2Fwww.cdc.gov%2Fepilepsy%2Fbasics%2Ffast-facts.htm [filed as EX2001 in IPR2019-00451, IPR2019-00450, IPR2019-00449].
Ericksson K, Kalviainen R. Pharmacologic management of convulsive status epilepticus in childhood. Expert Rev Neurotherapeutics 2005; 5: 777-783 [filed as EX1109 in IPR2019-00451].
European Communication for EP 12801372.9 mailed Jul. 5, 2016.
European Extended Search Report and Written Opinion for EP 09723906.5 mailed Jun. 3, 2013.
European Extended Search Report and Written Opinion for EP 12801372.9 mailed Mar. 26, 2015.
European Extended Search Report and Written Opinion for EP 18171484.1 mailed Oct. 30, 2018.
European Office Action for EP 08747813.7 dated Jun. 24, 2011.
European Office Action for EP 18171484.1 dated Apr. 6, 2020.
European Office Action for EP 18171484.1 dated May 17, 2021.
European Search Report and Written Opinion for EP 09835809 mailed Nov. 13, 2012.
European Summons to Attend Oral Proceedings with Annex for EP 12801372.9 dated May 16, 2017.
European Supplementary Search Report and Written Opinion for EP 08747813 mailed Jun. 22, 2010.
European Supplementary Search Report and Written Opinion for EP 11835002 mailed Jul. 7, 2015.
FDA Gui Final, Determining Whether to Submit an ANDA or a 505(b)(2) Application, Published May 2019, https://www.fda.gov/media/123567/download [filed as EX1146 in IPR2019-00451].
FDA Guidance for Industry (1999), Applications Covered by Section 505(b)(2), https://www.fda.gov/media/72419/download [filed as EX1148 in IPR2019-00451].
U.S. Appl. No. 18/062,062, filed Dec. 6, 2022.
Feen ES, Bershad EM, Suarez JI. Status Epilepticus. South Med J 2008; 101: 400-406 [filed as EX1106 in IPR2019-00451].
Fetih et al. "Improvement of Absorption Enhancing Effects of n-dodecy1-13-D-maltopyranoside by its colon-specific delivery using chitosan capsules" 2005, J. Pharmaceutics 293:127-135.
Fiest, K.M. et al., "Prevalence and Incidence of Epilepsy, A Systematic Review and Meta-Analysis of International Studies," Neurology 88, Jan. 17, 2017, pp. 296-303 [filed as EX2005 in IPR2019-00451, IPR2019-00450, IPR2019-00449].
File History for EP 128 01372.9, based on WO 2012/174158 and PCT/US2012/042311 [Part 1—pp. 1-250] [filed Jan. 29, 2019 as EX1040 in IPR2019-00541, IPR2019-00450, IPR2019-00449].
File History for EP 128 01372.9, based on WO 2012/174158 and PCT/US2012/042311 [Part 2—pp. 251-500] [filed Jan. 29, 2019 as EX1040 in IPR2019-00541, IPR2019-00450, IPR2019-00449].
File History for EP 128 01372.9, based on WO 2012/174158 and PCT/US2012/042311 [Part 3—pp. 501-662] filed Jan. 29, 2019 as EX1040 in IPR2019-00541, IPR2019-00450, IPR2019-00449].
File History for U.S. Appl. No. 12/413,439, filed Mar. 27, 2009 (439 FH) [Part 1—pp. 1-400] [filed as EX1007 in IPR2019-00451, IPR2019-00450, IPR2019-00449].

(56) References Cited

OTHER PUBLICATIONS

File History for U.S. Appl. No. 12/413,439, filed Mar. 27, 2009 (439 FH) [Part 2—pp. 401-800] [filed as EX1007 in IPR2019-00451, IPR2019-00450, IPR2019-00449].
File History for U.S. Appl. No. 12/413,439, filed Mar. 27, 2009 (439 FH) [Part 3—pp. 801-1200] [filed as EX1007 in IPR2019-00451, IPR2019-00450, IPR2019-00449].
File History for U.S. Appl. No. 12/413,439, filed Mar. 27, 2009 (439 FH) [Part 4—pp. 1201-1600] [filed as EX1007 in IPR2019-00451, IPR2019-00450, IPR2019-00449].
File History for U.S. Appl. No. 12/413,439, filed Mar. 27, 2009 (439 FH) [Part 5—pp. 1601-2000] [filed as EX1007 in IPR2019-00451, IPR2019-00450, IPR2019-00449].
File History for U.S. Appl. No. 12/413,439, filed Mar. 27, 2009 (439 FH) [Part 6—pp. 2001-2400] [filed as EX1007 in IPR2019-00451, IPR2019-00450, IPR2019-00449].
File History for U.S. Appl. No. 12/413,439, filed Mar. 27, 2009 (439 FH) [Part 7—pp. 2401-2800] [filed as EX1007 in IPR2019-00451, IPR2019-00450, IPR2019-00449].
File History for U.S. Appl. No. 12/413,439, filed Mar. 27, 2009 (439 FH) [Part 8—pp. 2801-3200] [filed as EX1007 in IPR2019-00451, IPR2019-00450, IPR2019-00449].
File History for U.S. Appl. No. 12/413,439, filed Mar. 27, 2009 (439 FH) [Part 9—pp. 3201-3488] [filed as EX1007 in IPR2019-00451, IPR2019-00450, IPR2019-00449].
File History for U.S. Pat. No. 8,895,546, U.S. Appl. No. 13/495,942 (546 FH) [Part 1—pp. 1-350] [filed Jan. 29, 2019 as EX1004 in IPR2019-00451, IPR2019-00450, IPR2019-00449].
File History for U.S. Pat. No. 8,895,546, U.S. Appl. No. 13/495,942 (546 FH) [Part 2—pp. 351-700] [filed Jan. 29, 2019 as EX1004 in IPR2019-00451, IPR2019-00450, IPR2019-00449].
File History for U.S. Pat. No. 8,895,546, U.S. Appl. No. 13/495,942 (546 FH) [Part 3—pp. 701-1050] [filed Jan. 29, 2019 as EX1004 in IPR2019-00451, IPR2019-00450, IPR2019-00449].
File History for U.S. Pat. No. 8,895,546, U.S. Appl. No. 13/495,942 (546 FH) [Part 4—pp. 1051-1400] [filed Jan. 29, 2019 as EX1004 in IPR2019-00451, IPR2019-00450, IPR2019-00449].
File History for U.S. Pat. No. 8,895,546, U.S. Appl. No. 13/495,942 (546 FH) [Part 5—pp. 1401-1750] [filed Jan. 29, 2019 as EX1004 in IPR2019-00451, IPR2019-00450, IPR2019-00449].
File History for U.S. Pat. No. 8,895,546, U.S. Appl. No. 13/495,942 (546 FH) [Part 6—pp. 1751-2100] [filed Jan. 29, 2019 as EX1004 in IPR2019-00451, IPR2019-00450, IPR2019-00449].
File History for U.S. Pat. No. 8,895,546, U.S. Appl. No. 13/495,942 (546 FH) [Part 7—pp. 2101-2450] (546 FH) [filed Jan. 29, 2019 as EX1004 in IPR2019-00451, IPR2019-00450, IPR2019-00449].
File History for U.S. Pat. No. 8,895,546, U.S. Appl. No. 13/495,942 (546 FH) [Part 8—pp. 2451-2681] [filed Jan. 29, 2019 as EX1004 in IPR2019-00451, IPR2019-00450, IPR2019-00449].
File History for U.S. Pat. No. 9,763,876, U.S. Appl. No. 14/527,613 (876 FH) [Part 1—pp. 1-270] [filed Jan. 29, 2019 as EX1002 in IPR2019-00451, IPR2019-00450, IPR2019-00449].
File History for U.S. Pat. No. 9,763,876, U.S. Appl. No. 14/527,613 (876 FH) [Part 2—pp. 271-530] [filed Jan. 29, 2019 as EX1002 in IPR2019-00451, IPR2019-00450, IPR2019-00449].
Fix "Oral controlled release technology for peptides: status and future prospects" Dec. 1996, Pharmaceutical Research13(12):1760-1764.
Florida Regional Common EMS Protocols Field Guide, Jones and Barlett Publishers, MA (2005) [filed as EX1069 in IPR2019-00451].
Food & Drug Administration, Grant Fast Track (IND 112621; NRL-1 (diazepam intranasal solution)) (Dec. 27, 2016) [filed as EX2002 in IPR2019-00451, IPR2019-00450, IPR2019-00449].
French et al., Pharmacopeial Standards and Specifications for Bulk Drugs and Solid Oral Dosage Forms. Journal of Pharmaceutical Sciences, 56(12) (Dec. 1967): 1622-1641 [filed as EX1033 in IPR2019-00451, IPR2019-00450, IPR2019-00449].
French J. and T. Pedley, "Initial Management of Epilepsy," New England Journal of Medicine 359: 166-176 (2008) [filed as EX2019 in IPR2019-00451].
Fricker et al. "Permeation enhancement of octreotide by specific bile salts in rats and human subjects: in vitro, in vivo correlations" 1996, Br. J. Pharmacol., 117(1):217-223.
Gizurarson et al., Intranasal Administration of Diazepam Aiming at the Treatment of Acute Seizures: Clinical Trials in Healthy Volunteers. Biological and Pharmaceutical Bulletin, vol. 22 Issue 4 (1999): 425-427 [filed as EX1030 in IPR2019-00451, IPR2019-00450, IPR2019-00449].
Gordon et al. "Nasal Absorption of Insulin: Enhancement by Hydrophobic Bile Salts" Nov. 1985, PNAS USA 82:7419-7423.
Greenblatt D, Gan L, Harmatz et al. Pharmacokinetics and pharmacodynamics of single-dose triazolam: EEG compared with digital symbol substitution test. Br J Clin Pharmacol 2005; 60: 244-248 [filed as EX1135 in IPR2019-00451].
Gudmundsdottir H, Sigurjonsdottir JF, Masson M et al., Intranasal administration of midazolam in a cyclodextrin based formulation: bioavailability and clinical evaluation in humans. Pharmazie 2001; 56: 963-966 [filed as EX1127 in IPR2019-00451].
Handbook of Pharmaceutical Excipients (Pharmaceutical Press and American Pharmacists Association, Publishers) (Fifth Edition, 2006) [filed as EX2029 in IPR2019-00451].
Harbord, M.G. et al., Use of intranasal midazolam to treat acute seizures in paediatric community settings. J Paediatr Child Health, 2004. 40(9-10):556-558 [filed as EX1142 in IPR2019-00451].
Hardman, et al, Editors, Goodman & Gilman's, The Pharmacological Basis of Therapeutics, 10th Edition (2001) [filed as EX1074 in IPR2019-00451].
Hathcox et al. "Inhibitory effects of sucrose fatty acid esters, alone and in combination with ethylenediaminetetraacetic acid and other organic acids, on viability of *Escherichia coli* 0157:H7" 1996, Food Microbiology 13(3):213-225.
Holsti M, Sill B, Firth S et al., Prehospital intranasal midazolam for the treatment of pediatric seizures. Ped Emerg Care 2007; 23: 148-153 [filed as EX1121 in IPR2019-00451].
Hovgaard et al. "Insulin Stabilization and GI Absorption" Mar. 1992, Journal of Controlled Release19(1-3):99-108.
Hovgaard et al. "Stabilization of insulin by Alkylmaltosides, B. Oral Absorption in Vivo in Rats" 1996, International Journal of Pharmaceutics, 132:115-121.
Hovgaard et al. "Stabilization of insulin by alkylmaltosides. A. Spectroscopic evaluation" 1996, International Journal of Pharmaceutics, 132(1-2):107-113.
Hovgaard et al."Insulin Stabilization and Gastrointestinal Absorption; Dissertation" Aug. 1991, Dept. Pharmaceutifcs, Univ. Utah.
Hussain A. et al. "Nasal Absorption of Propranolol in Humans," Journal of Pharmaceutical Sciences 69: 1240 (1980) [filed as EX2008 in IPR2019-00451].
Hussain et al. "Absorption enhancers in pulmonary protein delivery" Jan. 8, 2004, J Control Release 94(1):15-24.
Illum et al. "Nasal Drug Delivery—Recent Developments and Future Prospects" 2012, J. Controlled AH Release 161 (2):254-263.
Illum L. Is nose to brain transport of drugs a reality?. JPP 2004; 56: 3-17 [filed as EX1116 in IPR2019-00451].
Illum L. Nasal Clearance in Health and Disease. J Aerosol Med 2006; 19: 92-99 [filed as EX1113 in IPR2019-00451].
Illum L. Transport of drugs from the nasal cavity to the central nervous system. Eur J Pharm Sci 2000; 11: 1-18 [filed as EX1115 in IPR2019-00451].
Valtoco Evidence Spotlight document of 2020 (accessible online Mar. 5, 2020).
Wheless et al., "Safety of Valtoco (NRL-1; diazepam nasal spray) in Patients With Epilepsy: Interim Results From a Phase 3, Open-Label, 12-Month Repeat Dose Study", Amercian Epilepsy Society 2019 Annual Meeting, Dec. 6-10, 2019, Poster 1.224.
Smith B. Treatment of status epilepticus. Neurol Clin 2001; 19: 347-369 [filed as EX1108 in IPR2019-00451].
Stavem K, BJomaes H, Langmoen IA. Long-term seizures and quality of life after epilepsy surgery compared with matched controls. Neurosurgery 2008; 62: 326-334 [filed as EX1104 in IPR2019-00451].
Stevens et al. "Use of Glucagon to Treat Neonatal Low-Output Congestive Heart Failure after Maternal Labetalol Therapy", Jul. 1995, The Journal of Pediatrics 127(1):151-153 (abstract only).

(56) References Cited

OTHER PUBLICATIONS

Sun et al. "Nasal spray for curing status epilepticdus (SE) ad eples, comprises alprazolam and carriers" Thompson Scientific Database WPI, Section Ch., week 200164 Abstract.
Swarbrick et al. "Encyclopedia of Pharmaceutical Technology", 2002, Informa Health Care, 2nd edition, 1:918.
Table of Various Diazepam Solutions Described in or Modified From Sonne's Example 11 (undated) [filed Jan. 29, 2019 as EX1050 in IPR2019-00451, IPR2019-00450].
Terry D. et al., "Acceptance of the Use of Diazepam Rectal Gel in School and Day Care Settings," Journal of Child Neurology 22: 1135-1138 (2007) [filed as EX2016 in IPR2019-00451].
Tillman et al. "Oral Delivery of Antisense Oligonucleotide i Man" 2008, J. Pharm. Sci. 97.1:225-236 (Published online Aug. 22, 2007).
Transcript of Telephone Conference on Feb. 11, 2020 [filed as EX2027 in IPR2019-00451].
Transcript of the Jan. 14, 2020 deposition of Dr. Gizararson [filed as EX1149 in IPR2019-00451].
Tsuchido et al."Lysis of Bacillus subtilis Cells by Glycerol and Sucrose Esters of Fatty Acids", 1987, Applied and Environmental Microbiology 53(3):505-508.
Turker et al. "Nasal route and drug delivery systems" 2004, Pharm. World Sci. 26(3):137-142.
Turton et al. "A role for glucagon-like peptide-1 in the central regulation of feeding" 1996; Nature 379:69-72.
U.S. Final Office Action for U.S. Appl. No. 14/948,081 mailed Apr. 10, 2019.
U.S. Office Action for U.S. Appl. No. 13/371,274 mailed Apr. 10, 2013.
U.S. Office Action for U.S. Appl. No. 13/371,274 mailed Sep. 26, 2012.
U.S. Office Action for U.S. Appl. No. 13/495,942 mailed Oct. 1, 2013.
U.S. Office Action for U.S. Appl. No. 14/021,988 mailed May 22, 2015.
U.S. Office Action for U.S. Appl. No. 14/152,686 mailed Aug. 25, 2015.
U.S. Office Action for U.S. Appl. No. 14/152,686 mailed Dec. 31, 2014.
U.S. Office Action for U.S. Appl. No. 14/152,686 mailed Jul. 5, 2016.
U.S. Office Action for U.S. Appl. No. 14/948,081 mailed Feb. 15, 2018.
U.S. Office Action for U.S. Appl. No. 14/948,081 mailed Jun. 20, 2017.
U.S. Office Action for U.S. Appl. No. 14/948,081 mailed Oct. 31, 2016.
U.S. Office Action for U.S. Appl. No. 15/470,498 mailed Apr. 12, 2018.
U.S. Office Action for U.S. Appl. No. 12/116,842 mailed Apr. 2, 2013.
U.S. Office Action for U.S. Appl. No. 12/116,842 mailed Dec. 17, 2013.
U.S. Office Action for U.S. Appl. No. 12/116,842 mailed Jul. 8, 2015.
U.S. Office Action for U.S. Appl. No. 12/116,842 mailed May 25, 2011.
U.S. Office Action for U.S. Appl. No. 12/116,842 mailed Nov. 15, 2011.
U.S. Office action for U.S. Appl. No. 12/266,529 mailed Jul. 10, 2012.
U.S. Office action for U.S. Appl. No. 12/266,529 mailed Nov. 16, 2011.
U.S. Office action for U.S. Appl. No. 12/413,439 mailed Jul. 14, 2016.
U.S. Office action for U.S. Appl. No. 12/413,439 mailed Jun. 19, 2014.
U.S. Office action for U.S. Appl. No. 12/413,439 mailed Mar. 13, 2015.
U.S. Office action for U.S. Appl. No. 12/413,439 mailed Mar. 18, 2011.
U.S. Office action for U.S. Appl. No. 12/413,439 mailed Mar. 30, 2017.
U.S. Office action for U.S. Appl. No. 12/413,439 mailed Nov. 21, 2011.
U.S. Office action for U.S. Appl. No. 12/413,439 mailed Oct. 19, 2017.
U.S. Office action for U.S. Appl. No. 12/413,439 mailed Oct. 5, 2015.
U.S. Office Action for U.S. Appl. No. 15/955,397 dated Mar. 20, 2020.
U.S. Office Action for U.S. Appl. No. 15/470,498 dated May 5, 2020.
U.S. Office Action for U.S. Appl. No. 15/470,498 dated Nov. 2, 2018.
U.S. Office Action for U.S. Appl. No. 15/470,498 dated Sep. 12, 2019.
U.S. Office Action for U.S. Appl. No. 16/594,897 dated Apr. 9, 2021.
U.S. Office Action for U.S. Appl. No. 14/527,613 mailed Apr. 21, 2017.
U.S. Office Action for U.S. Appl. No. 14/527,613 mailed Jul. 14, 2016.
U.S. Appl. No. 60/148,464, filed Aug. 12, 1999.
U.S. Appl. No. 60/632,038, filed Nov. 30, 2004 [filed as EX1065 in IPR2019-00451, IPR2019-00450].
U.S. Appl. No. 61/040,281, filed Mar. 28, 2008 [filed as EX1046 in IPR2019-00451, IPR2019-00450, IPR2019-00449].
Neurelis Clinical Pharmacology Review for Valtoco (43 pages) by Center for Drug Evaluation and Research, 2019.
Hogan et al. "Bioavailability and Safety of Diazepam Intranasal Solution Compared to Oral and Rectal Diazepam in Healthy Volunteers" 2020, Epilepsia pp. 455-464.
HHS (Texas) Midazolam (Nayzilam) nasal spray, CIV, Description (10 pages) 2020.
Kay et al. "Intranasal midazolam as first-line inhospital treatment for status epilepticus: a pharmaco-EEG cohort study" 2019, Annals of Clinical and Translational Neurology 6(12);2413-2425.
Prescribing Information for Nayzliam (p. 1-25) (Year: 2023).
Seizures Information, 2023 Icahn School of Medicine at Mount Sinai (10 pages).
Illum, Nasal drug delivery-possibilities, problems and solutions. Journal of Controlled Release 87 (2003): 187-198 [filed as EX1027 in IPR2019-00451, IPR2019-00450, IPR2019-00449].
International Preliminary Report on Patentability and Written Opinion for PCT/US2008/062961 mailed Nov. 10, 2009.
International Preliminary Report on Patentability and Written Opinion PCT/US2009/38696 International Preliminary Report on Patentability dated Sep. 28, 2010.
International Seach Report and Written Opinion for PCT/US2012/042311 mailed Aug. 31, 2012.
International Search Report and Written Opinion for PCT/US2008/062961 mailed Jul. 25, 2008.
International Search Report and Written Opinion for PCT/US2009/038696 mailed Sep. 28, 2009.
International Search Report and Written Opinion for PCT/US2014/070944 mailed Apr. 15, 2015.
International Search Report and Written Opinion from PCT/US2011/056735 dated Jun. 20, 2012.
Ivaturi et al., Pharmacokinetics and tolerability of intranasal diazepam and midazolam in healthy adult volunteers. Acta Neurol Scand., 120(5) (Nov. 2009): 353-357. doi: 10.1111/j.1600-0404.2009.01170.x. Epub May 14, 2009 [filed as EX1028 in IPR2019-00451, IPR2019-00450, IPR2019-00449].
Japanese Decision of Refusal for JP 2010-507633 dated Jul. 9, 2013.
Japanese Office Action for JP 2010-507633 dated Oct. 23, 2012.
Japanese Office Action for JP 2019-083274 dated Mar. 25, 2020.
Japanese Office Action for JP 2019-083274 dated Nov. 18, 2020.
Japanese Office Action for JP 2014-515967 dated Apr. 24, 2017.
Japanese Office Action for JP 2014-515967 dated Mar. 30, 2016.
Japanese Office Action for JP 2014-515967 dated Nov. 28, 2016.
Japanese Office Action for JP 2017-185485 dated Jul. 2, 2018.

(56) References Cited

OTHER PUBLICATIONS

Jeannet, P.Y. et al., Home and hospital treatment of acute seizures in children with nasal midazolam. Eur J Paediatr Neurol, 1999. 3(2):73-77 [filed as EX1143 in IPR2019-00451].
Judgment Final Written Decision filed Aug. 6, 2020 in IPR2019-00451.
Katzung "Basic and Clinical Pharmacology. 7th edition" 1998, Appleton & Lange: Stamford, Connecticut, pp. 34-49.
Kibbe, editor, Handbook of Pharmaceutical Excipients. Third Edition, American Pharmaceutical Association, Washington DC (2000) [filed as EX1026 in IPR2019-00451, IPR2019-00450, IPR2019-00449].
Kissel et al. "Tolerability and absorption enhancement of intranasally administered octreotide by sodium taurodihydrofusidate in healthy subjects." Jan. 1992, Pharm Res. 9(1):52-57.
Kite et al. "Use of in vivo-generated biofilms from hemodialysis catheters to test the efficacy of a novel antimicrobial catheter lock for biofilm eradication in vitro" Jul. 2004, J Clin Microbiol. 42(7):3073-3076.
Knoester et al., Pharmacokinetics and pharmacodynamics of midazolam administered as a concentrated intranasal spray. A study in healthy volunteers. Br J Clin Pharmacol, 53(5) (May 2002): 501-507 [filed as EX1043 in IPR2019-00451, IPR2019-00450, IPR2019-00449].
Knudsen "Glucagon-like Peptide-1: The Basis of a New Class of Treatment for Type 2 Diabetes" 2004; J. Med. Chem., 47:4128-4134.
Lacy et al. "Drug Information Handbook, 7th Edition 1999-2000" 1999, Lexi-Comp, Inc. pp. 163-164.
Lahat E, Goldman M, Barr J et al. Comparison of intranasal midazolam with intravenous diazepam in treating febrile seizures in children: prospective randomized study. BMJ 2000; 321: 83-87 [filed as EX1139 in IPR2019-00451].
Lahat et al. "Intranasal midazolam for childhood seizures" 1998; The Lancet 352:620.
Lau S. and J. Slattery, "Absorption of Diazepam and Lorazepam Following Intranasal Administration," International Journal of Pharmaceutics, 54: 171-174 (1989) [filed as EX2009 in IPR2019-00451].
Lehninger et al. "Principles of Biochemistry with an Extended Discussion of Oxygen-Binding Proteins", 1982, Worth Publishers, Inc., pp. 150-151.
Lewine, M.D., Howard, Quick Injection Helps Stop Epileptic Seizures, Harvard Health Blog (Feb. 23, 2012), available at https://www.health.harvard. edu/blog/quick-injection-helps-stop-epileptic-seizures-201202234319/print/ [filed as EX2003 in IPR2019-00451, IPR2019-00450, IPR2019-00449].
Lindhardt et al., Electroencephalographic effects and serum concentrations after intranasal and intravenous administration of diazepam to healthy volunteers. Blackwell Science Ltd Br J Clin Pharmacol, 52 (2001): 521-527 [filed as EX1025 in IPR2019-00451, IPR2019-00450, IPR2019-00449].
Liu et al. "Interaction between chitosan and alkyl P-D-glucopyranoside and its effect on their antimicrobial activity" 2004, Carbohydrate Polymers, 56:243-250.
Loftsson T, Gudmundsdottir H, Sigurjonsdottir JF et al. Cyclodextrin solubilization of benzodiazepines: formulation of midazolam nasal spray. Int J Pharm 2001; 212:29-40 [filed as EX1125 in IPR2019-00451].
Logroscino G, Hessdorffer DC, Cascino G et al. Time trends in incidence, mortality, and case-fatality after first episode of status epilepticus. Epilepsia 2001; 42: 1031-1035 [filed as EX1105 in IPR2019-00451].
Lowenstein DH, Alldredge BK. Status epilepticus. N Eng J Med 1998; 338: 970-976 976 [filed as EX1101 in IPR2019-00451].
Lowenstein DH, Bleck T, Macdonald RL. It's time to revise the definition of status epilepticus. Epilepsia 1999; 40: 120-122 [filed as EX1102 in IPR2019-00451].
Maa et al. "Biopharmaceutical powders: particle formation and formulation considerations" 2000, Curr. Pharm. Biotechnol., 1(3):283-302.
Mahmoudian T, Zadeh M. Comparison of intranasal midazolam with intravenous diazepam for treating acute seizures in children. Epilepsy and Behavior 2004; 5: 253-255 [filed as EX1138 in IPR2019-00451].
Maitani et al., Design of ocular/lacrimal and nasal systems through analysis of drug administration and absorption. Journal of Controlled Release, 49(2-3) (Dec. 15, 1997): 185-192 [filed as EX1045 in IPR2019-00451, IPR2019-00450, IPR2019-00449].
Mark et al. "GLP-1: target for a new class of antidiabetic agents?" 2004, J. R. Soc. Med. 97(6):270-274.
Material Safety Data Sheet for Anatrace, Inc. product n-Dodecyl-.beta.-d-Maltopyranoside, Anagrade, Dated: Jan. 25, 1994 and Revised: Jul. 15, 2004, hhtp://media.affymetrix.com/estore/browse/level.sub.-three)category.sub.---and.sub.-products.jsp?category=35843&categoryIdClicked=35843&expand=tru- e&parent=35900, access online on Dec. 13, 2012 (poster).
Mathew "Serotonin 1D (5-HT1D) agonists and other agents in acute migraine" 1997, Neurol. Clin. 15(1):61-83.
Matsumura et al. "Surface activities, biodegradability and antimicrobial properties of n-alkyl glucosides, mannosides and galactosides" 1990, Journal of the America Oil Chemists' Society 67(12):996-1001.
Meierkord H, Engelsen B, Gocke K et al. EFNS guideline on the management of status epilepticus. Eur J Neurol 2006; 13: 445-450 [filed as EX1111 in IPR2019-00451].
Merkus F, van den Berg MP. Can nasal drug delivery bypass the blood-brain barrier? Questioning the direct transport theory. Drugs 2007; 8:133-144 [filed as EX1117 in IPR2019-00451].
Merkus P, Ebbens FA, Muller B, Fokkens WJ. Influence of anatomy and head position on intranasal drug deposition. Eur Arch Otorhinolaryngol 2006; 263: 827-832 [filed as EX1114 in IPR2019-00451].
Mitrano et al. "Factors Affecting Insulin Adherence to Type I Glass Bottles" 1982, Am. J. Hasp.. Pharm. 39.9:1491-1495.
Mittal P, Manohar R, Rawat A. Comparative study of intranasal midazolam and intravenous diazepam sedation for procedures and seizures. Ind J Pediatrics (2006)73: 975-978 [filed as EX1137 in IPR2019-00451].
Moses et al. "Insulin Administered Intranasally as an Insulin-Bite Salt Aerosol-Effectiveness and Reproducibility in Normal and Diabetic Subjects" Nov. 1983, Diabetes, 32:1040-1047.
Agarwal et al. "A Pilot Study Assessing the Bioavailability and Pharmacokinetis of Diazepam after Intranasal and Intravenous Administration in Healthy Volunteers" 2013, Epilepsy Research 105:362-367.
Asnis-Alibozek et al. "The unmet need for rapid epileptic seizure termination (REST)" Nov. 25, 2020, Epilepsy Behavior Reports, 15:1-6.
European Search Report and Written Opinion for application No. EP 22737150.7 dated Mar. 20, 2025.
European Search Report and Written Opinion for application No. EP 22821085.2 dated Mar. 5, 2025.
Lopez-Toledano et al. "Study Design of an Open-Label Pharmacokinetic and Safety Trial of Diazepam Nasal Spray (Valtoco) in Children 2-5 Years Old with Seizure Clusters" Nov. 22, 2021, Abstracts, American Epilepsy Society Annual Meeting.
Penovich et al. "Examining the patient and caregiver experience with diazepam nasal spray for seizure clusters: Results from an exit survey of a phase 3, open-label, repeat-dose safety study" May 19, 2021, Epilepsy and Behavior, Academic Press, San Diego, CA, US, 121:1-7.
Japanese Office Action for application No. JP 2021-078241 dated Jun. 23, 2025.
Abou-Khalil et al. "A double-blind, randomized, placebo-controlled trial of a diazepam auto-injector administered by caregivers to patients with epilepsy who require intermittent intervention for acute repetitive seizures" Sep. 2013, Epilepsia, 54(11):1968-1976.
Higdon et al. "A review of a diazepam nasal spray for the treatment of acute seizure clusters and prolonged seizures" Aug. 2021, Expert Review of Neurotherapeutics, 21(11):1207-1212.
Li et al. "Development of an ethyl laurate-based microemulsion for rapid-onset intranasal delivery of diazepam" 2002, Int J Pharmaceutics, 237:77-85.

(56)             References Cited

OTHER PUBLICATIONS

Partial European Search Report and Invitation to Pay Additional Fees for EP 22737150.7 dated Nov. 22, 2024 (15 pages).

Pharmacopeial Forum, vol. 30, No. 1, Jan.-Feb. 2004, pp. 96-97.

Sperling et al. "Dosing feasibility and tolerability of intranasal diazepam in adults with epilepsy" Aug. 2014, Epilepsia, 55(10):1544-1550.

Final Office Action mailed on May 14, 2025, for U.S. Appl. No. 18/782,646. 22 pages.

"Intranasal Midazolam Administration—Dosage and How to Use", Intranasal midazolam administration, Benzodiazepines, Aug. 16, 2017; 4 pages, Retrieved from Internet: URL: https://www.singhealth.com.sg/patient-care/medicine/intranasal-midazolam-administration.

"Memorandum for Review of Revised Label and Labeling for Valtoco (diazepam) Spray"; Center for Drug Evaluation and Research for Application No. 2116350rig1s000 dated Jan. 6, 2020, 141 pages.

Non-Final Office Action mailed May 15, 2025, for U.S. Appl. No. 18/405,628. 102 pages.

"Validity of Outcome Measures—Brivaracetam (Briviera)"; Appendix 5; NCBI Bookshelf; Canadian Agency for Drugs and Technologies in Health, 2017; 5 pages. Retrieved from url: https://www.ncbi.nlm.nih.gov/books/NBK447903/?report=prinlable.

Chinese Office Action for application No. CN 201710940124.1 dated Aug. 28, 2025. (with Machine Translation).

Decision Granting Inter Partes Review of U.S. Pat. No. 11,241,414 (IPR2025-00465) dated Sep. 16, 2025, 38 pages.

Decision Granting Inter Partes Review of U.S. Pat. No. 11,793,786 (IPR2025-00466) dated Sep. 16, 2025, 40 pages.

Decision Granting Inter Partes Review of U.S. Pat. No. 8,895,546 (IRP2025-00464) dated Sep. 16, 2025, 23 pages.

Penovich et al. "Acute Repetitive Seizures (ARS) or Cluster Seizures," Clinician's Corner, Jan. 14, 2020, 5 pages.

Japanese Office Action for Application No. 2023-541507 dated Jan. 5, 2026. (with Machine Translation).

Notice of Allowance issued Oct. 17, 2025 for U.S. Appl. No. 18/782,646, 25 pages.

* cited by examiner

METHODS AND COMPOSITIONS FOR TREATING SEIZURE DISORDERS IN PEDIATRIC PATIENTS

CROSS-REFERENCE TO RELATED APPLICATION

This application claims the benefit of U.S. Provisional Application Ser. No. 63/209,092, entitled "Methods and Compositions for Treating Seizure Disorders in Pediatric Patients", filed on Jun. 10, 2021, the entire contents of which are incorporated herein by reference in their entirety for all purposes.

FIELD

The present disclosure relates generally to compositions comprising a benzodiazepine and an alkyl maltoside, suitable for intranasal administration to a pediatric patient and effective to treat seizures and seizure disorders in said pediatric patient.

BACKGROUND

Epilepsy is a significant health problem affecting 50 million people worldwide, including 2.7 million Americans. Epilepsy has a bimodal distribution with peaks in infancy/early childhood and in the elderly. About one third of all patients with epilepsy remain drug resistant despite numerous approved chronic oral therapies with a broad range of mechanisms of action. Epilepsy negatively impacts quality of life and increases morbidity and mortality. In the US, 25-50,000 deaths each year are attributed to seizures and related causes.

Seizure emergencies include acute repetitive seizures (ARS, also known as a seizure cluster), which are defined as intermittent increases of seizure activity while on stable regimens of anti-seizure drugs (ASDs). Pediatric patients with epilepsy are often prone to seizure clusters, especially patients with severe early onset developmental and epileptic encephalopathies. Seizure clusters during childhood often portend a poor neurological outcome. The intravenous (IV) formulation of diazepam has been used for over 50 years in the treatment of seizure emergencies, including status epilepticus. The current options for treatment of ARS include a VALTOCO® and rectal gel formulation of diazepam, DIASTAT®.

Intranasal diazepam (VALTOCO®) was approved in 2020 for marketing by the United States (US) Food and Drug Administration (FDA) and is indicated for the acute treatment of intermittent, stereotypic episodes of frequent seizure activity (i.e., seizure clusters, ARS) that are distinct from a patient's usual seizure pattern in patients with epilepsy 6 years of age and older.

DIASTAT® was approved in 1997 and is intended for rectal administration in the management of selected, refractory, patients with epilepsy, on stable regimens of AEDs, who require intermittent use of diazepam to control bouts of increased seizure activity and is approved for use in patients 2 years of age and older. Experience in clinical trials and post-marketing surveillance has demonstrated an excellent safety profile for DIASTAT® with few significant side effects reported. Despite the safety and effectiveness of DIASTAT®, the use is limited by social and legal restrictions related to the route of administration. Additionally, rectal administration of diazepam results in a highly variable dose due to inconsistent absorption and the potential of bowel movements which may necessitate an additional dose if part of the initial dose is expelled. Due to this route of administration, the use of DIASTAT® has been limited primarily to the pediatric population, ages 2-12 years.

SUMMARY

In one aspect, the present disclosure provides a method of treating a pediatric subject having a seizure disorder. This method comprises administering, to a pediatric subject that is 2 to 5 years old, a composition comprising an effective amount of diazepam, an alkyl maltoside, and a carrier system comprising one or more natural or synthetic tocopherols or tocotrienols and one or more alcohols. The composition is administered to a nasal mucosal membrane of the pediatric subject to treat the seizure disorder in the pediatric subject.

In another aspect, the present disclosure provides a method of treating recurrent seizures in a pediatric subject in need thereof. This method comprises administering, to a pediatric subject that is 2 to 5 years old, a composition comprising an effective amount of diazepam, an alkyl maltoside, and a carrier system comprising one or more natural or synthetic tocopherols or tocotrienols and one or more alcohols to a nasal mucosal membrane of the pediatric subject during or before a seizure.

Diazepam nasal spray (Valtoco®) is approved for acute treatment of seizure clusters in patients with epilepsy aged ≥6 years. A previous pharmacokinetic (PK) study showed diazepam nasal spray had similar bioavailability, but less interpatient variability compared with diazepam rectal gel in healthy adult volunteers. In a study of patients aged 6-65 years with epilepsy, diazepam nasal spray showed similar PK profiles in interictal versus ictal/peri-ictal periods. In a long-term phase 3 safety study of patients aged 6-65 years, diazepam nasal spray had a safety profile consistent with that of rectal gel.

Younger children also may require out-of-hospital treatment for seizure clusters. There are limited data on the PK of diazepam in children, with no pediatric data available for rectal gel, which is approved for patients aged ≥2 years. Diazepam nasal spray represents another diazepam formulation that may be easier to use and could potentially provide more predictable blood levels than rectal gel in this population.

DETAILED DESCRIPTION

Before the present compositions and methods are described, it is to be understood that various aspects of intranasal benzodiazepine compositions and methods of their use are disclosed herein. Unless indicated otherwise, all technical and scientific terms used herein have the meaning commonly understood by one of ordinary skill in the art. It is also to be understood that the terminology used in the description is for the purpose of describing the particular aspects or embodiments only and is not intended to limit the scope. The disclosed intranasal compositions, method of their manufacture, and methods of their use are not strictly limited to the particular compositions, processes, or methods described, as these can vary to an extend one of skill in the art will recognize without diverging from the benefits and advantages imparted by the compositions and methods. Though one of skill in the art will readily recognize obvious variations and substitutions that may be made to accomplish the same result through equivalent means or function, tor the purpose of describing the various aspects and embodiments of intranasal benzodiazepine compositions, methods of their manufacture, and methods of their use, preferred compositions and methods are now described.

The compositions disclosed herein are suitable for administration to the nasal cavity. As such, the phrases "intranasal solution," "intranasal composition," and "intranasal formulation" are used interchangeably to mean a composition suitable for administration to the nasal mucosal membranes which line the nasal cavity.

As used herein, the term "subject" and "patient" expressly includes humans and non-human mammalian subjects. The term "non-human mammal" as used herein extends to, but is not restricted to, household pets and domesticated animals. Non-limiting examples of such animals include primates, cattle, sheep, ferrets, mice, rats, swine, camels, horses, poultry, fish, rabbits, goats, dogs and cats. As used herein, the term "pediatric" refers to a subject of age 2 to 5, inclusive.

As used herein, "treating" and other grammatical forms thereof (e.g., treat, treatment) may improve symptoms of a seizure disorder or of an acute seizure. Improvement may include reducing the frequency, length, or severity of the acute seizure or of recurring episodes of seizures.

In any embodiment, the methods and compositions disclosed herein may comprise the recited steps and components. As used here, "comprise" is open language used to recite steps or components that are included in the recited method or composition but to indicate that other elements may also be included, even though said elements are not explicitly recited. In any embodiment, the methods and compositions disclosed herein may consist essentially of the recited steps and components. As used here, "consist essentially of" is used to recite steps or components that are included in the recited method or composition and to indicate that other elements may also be included but said other elements would not materially affect the properties of the composition or the results of the method. In any embodiment, the methods and compositions disclosed herein may consist of the recited steps and components. As used here, "consist of" is closed language used to recite steps or components that are included in the recited method or composition and that no other elements are included other than those explicitly recited. Any use of the term comprise, comprises or comprising may be replaced with "consisting essentially of" or "consisting of."

Surprisingly, administration of a benzodiazepine to the nasal mucosal membranes of a pediatric subject via the various intranasal compositions, as disclosed herein, induces a therapeutic benefit to the pediatric subject substantially earlier than would be expected based on measured systemic levels of the benzodiazepine. A therapeutic effect is not only experienced by the pediatric subject, but measured via EEG well before (e.g., less than 2 minutes after administration) the systemic concentration of benzodiazepine reaches therapeutically relevant levels. As used herein, the term "pharmacodynamic" or "PD" is used to describe qualitative effects the administered benzodiazepine has on the pediatric subject, such as a change in EEG data, a change in seizure length or severity, a change in symptoms associated therewith, or a change associated with side effects caused by the administered benzodiazepine. The term "pharmacokinetic" or "PK" is used to describe, quantitatively, movement and processing of the benzodiazepine drug by the pediatric subject's body, such as plasma concentrations of the drug and any metabolites thereof (e.g., $C_{max}$, $T_{max}$), bioavailability, half-life, and the like. While various aspects of the PK profile of a benzodiazepine administered intranasally via the intranasal compositions as disclosed herein are similar to aspects of the PK profile of a benzodiazepine administered intravenously (e.g., similar AUC and bioavailability) and orally (e.g., similar $C_{max}$ and $T_{max}$), many of the adverse side effects associated with IV, oral, and rectal administration of benzodiazepines, such as somnolence, headaches, and depression/suicidal thoughts and behaviors, are reduced. Therefore, the intranasal compositions and methods of their use as provided herein represent a substantial improvement in the treatment of seizures and seizure disorders, both in the rapid realization of therapeutic benefit after administration and in improved patient compliance after experiencing reduced unpleasant side effects.

Compositions

As such, in one aspect, the present disclosure provides a composition suitable for intranasal administration ("intranasal composition") comprising: a therapeutically effective amount of a benzodiazepine drug; about 0.01% w/v to about 1% w/v of an alkyl maltoside; and a carrier system comprising about 30% w/v to about 90% w/v of a natural or synthetic tocopherol, a natural or synthetic tocotrienol, or a combination thereof and about 10% w/v to about 70% w/v of one or more alcohols.

Benzodiazepines have the general basic structure of formula I:

Formula I

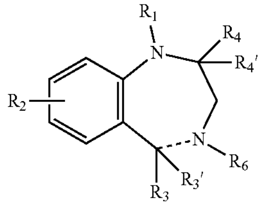

wherein $R_1$-$R_5$ are substitutable chemical moieties. $R_1$ may be an optionally substituted alkyl or may form a optionally substituted heterocyclic ring with $R_4$ (where the hetero atom is the nitrogen (N) in the diazepine ring); $R_2$ is a halogen (e.g., Cl, Br); $R_3$ may be an optionally substituted aryl group (e.g., 2-chloro or 2-fluorophenyl); $R_5$ is —H or —OH; if $R_4$ is not joined with $R_1$ to form an optionally substituted heterocyclic ring, $R_4$ and $R_4$' may together form a carbonyl moiety (C═O) with the carbon to which they are attached; $R_3$' and $R_6$ may together form a double bond or may be combined to form an optionally substituted heterocyclic ring fused to the diazepine ring at the atoms to which they are attached. Benzodiazepines are basic compounds, and as such, may form acid addition salts with pharmaceutically acceptable acids, such as pharmaceutically acceptable mineral acids and pharmaceutically acceptable organic acids. Reference to a benzodiazepine herein refers to and includes any pharmaceutically acceptable form, such as the free base form, an acid addition salt, a base addition salt, or a solvated form (such as a hydrate).

Pharmaceutically acceptable mineral acids include hydrochloric acid, sulfuric acid, sulfurous acid, phosphoric acid, phosphorous acid, and others that will be recognized by those of skill in the art. Pharmaceutically acceptable organic acids include acetic acid, benzoic acid, tartaric acid, citric acid, oxalic acid, maleic acid, malonic acid, 1-hydroxy-2- naphthoic acid, 2,2-dichloroacetic acid, 2-hydroxyethanesulfonic acid, 2-oxoglutaric acid, 4-acetaidobenzoic acid, 4-aminosalicylic acid, acetic acid, adipic acid, ascorbic acid (L), aspartic acid (L), benzenesulfonic acid, benzoic acid, camphoric acid (+), caphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (–L), malonic acid, mandelic acid (DL), methanesulfonic acid, benzenesulfonic acid (besylic acid), naphthalene-1,5-disulfonic acid, naphthalene-2-sulfonic acid, nicotinic acid, nitric acid, oleic acid, oxalic acid, palmitic acid, pamoic acid, phosphoric acid, propionic acid, pyroglutamic acid (–L), salicylic acid, sebacic acid, stearic acid, succinic acid, sulfuric acid, tartaric acid (+L), thiocyanic acid, toluenesulfonic acid (p), and undecylenic acid. Other pharmaceutically acceptable acids may be pharmaceutically acceptable acidic (anionic) polymers or pharmaceutically acceptable amphoteric polymers. One skilled in the art will recognize that other basic active pharmaceutical ingredients may be combined with the foregoing acids to produce acid addition salts.

Examples of benzodiazepines that may be delivered intranasally via the intranasal compositions as disclosed herein include, but are not limited to, alprazolam, brotizolam, chlordiazepoxide, clobazam, clonazepam, clorazepam, demoxazepam, diazepam, flumazenil, flurazepam, halazepam, olanzapine, midazolam, nordazepam, medazepam, nitrazepam, oxazepam, lorazepam, prazepam, quazepam, triazolam, temazepam, loprazolam, any pharmaceutically acceptable salt thereof, as well as any combinations thereof. For example, particularly useful compositions may comprise diazepam, midazolam, lorazepam, or a pharmaceutically acceptable salt thereof. Diazepam is chemically known as 7-chloro-1,3-dihydro-1-methyl-5-phenyl-1,4-benzodiazepin-2-one and is shown below in Formula II.

Formula II

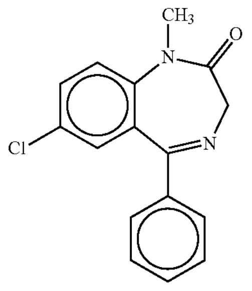

Compositions for delivering a benzodiazepine intranasally ("intranasal compositions") comprise a therapeutically effective amount of a benzodiazepine, for example, about 1 mg to about 20 mg of the benzodiazepine per a volume of about 10 μL to 200 μL. For example, an intranasal composition may comprise about 5 mg/mL (0.5% w/v) to about 0.6 g/mL (60% w/v) or about 10 mg/mL to about 250 mg/mL of a benzodiazepine, which also includes concentrations of about 1% w/v to about 50% w/v, about 5% w/v to about 25% w/v, or about 5% w/v to about 15% w/v of a benzodiazepine. These ranges include any discreet concentrations within the disclosed ranges, such as, about 5% w/v, about 7.5% w/v, about 10% w/v, about 15% w/v, and about 20% w/v of a benzodiazepine.

The intranasal compositions as disclosed herein comprise a benzodiazepine dissolved in a carrier system comprising a natural or synthetic tocopherol, a natural or synthetic tocotrienol, or a combination thereof and one or more alcohols.

The intranasal compositions may comprise about 30% w/v to about 90% w/v of a natural or synthetic tocopherol, a natural or synthetic tocotrienol, or a combination thereof, such as about 50% w/v to about 75% w/v, about 50% w/v to about 60% w/v, about 45% w/v to about 65% w/v, about 45% w/v to about 85% w/v, or about 10% w/v to about 25% w/v of a natural or synthetic tocopherol, a natural or synthetic tocotrienol, or a combination thereof.

Examples of suitable natural or synthetic tocopherols or tocotrienols include, but are not limited to, α-tocopherol, β-tocopherol, γ-tocopherol, δ-tocopherol, α-tocotrienol, β-tocotrienol, γ-tocotrienol, δ-tocotrienol, tocophersolan, an isomer of any thereof, an ester of any thereof, an analog or derivative of any thereof, and any combination thereof. A synthetic tocopherol may be covalently bonded to a glycol polymer, such as polyethylene glycol, as in vitamin E TPGS (vitamin E polyethylene glycol succinate). Alternatively, the intranasal compositions as disclosed herein may be free of, or substantially free of, such glycol-bound synthetic tocopherols. Many of the various tocopherol and tocotrienols solvents described above are naturally occurring vitamin E compounds or vitamin E esters. Vitamin E is a class of fat-soluble methylated phenols. As used herein, vitamin E refers to any of the natural or synthetic tocopherols, tocotrienols, isomers thereof, esters thereof, or any analogs or derivatives thereof, as well as combinations thereof. It has been found that vitamin E is an effective carrier for benzodiazepines and does not irritate sensitive mucosal membranes. Typically, vitamin E is considered hydrophobic and, as such, is used in emulsion-type compositions which tend to be unstable. However, when including a vitamin E carrier with one or more lower alcohols, a composition may be provided having enhanced stability and suitability as a carrier for intranasal administration of a benzodiazepine.

Therefore, the carrier system of the intranasal compositions disclosed herein also comprises about 10% w/v to about 70% w/v of one or more alcohols. As used herein, "alcohol" is used to describe a molecule having at least one hydroxyl functional group (—OH) bound to a saturated carbon atom, which includes monohydric alcohols and polyhydric alcohols, such as glycols. The alcohol may be a lower alcohol, which includes compounds with six or fewer carbon atoms, such as ethanol, propanol, butanol, pentanol, benzyl alcohol, ethylene glycol, propylene glycol, butylene glycol, pentylene glycol, any isomer thereof, or any combination thereof. An intranasal composition may comprise about 10% w/v to about 70% w/v of one or more alcohols such as about 15% w/v to about 55% w/v, or about 25% w/v to about 40% w/v, or about 30% w/v of one or more alcohols. For example, an intranasal composition may comprise 15% w/v to about 55% w/v, or about 25% w/v to about 40% w/v, or about 30% w/v of benzyl alcohol, ethanol, or a mixture thereof. In another example, an intranasal composition may comprise a mixture of ethanol and benzyl alcohol. In any embodiment, an intranasal composition may comprise about 10% w/v to about 25% w/v of ethanol and about 5% w/v to about 15% w/v of benzyl alcohol, or about 15% w/v to about 22.5% w/v ethanol and about 7.5% w/v to about 12.5% w/v benzyl alcohol, or about 10% w/v to about 25% w/v ethanol and about 7.5% w/v to about 12.5% w/v benzyl alcohol, or about 17% w/v to about 20% w/v ethanol and about 10% w/v to about 12% w/v benzyl alcohol. In any embodiment, an intranasal composition may comprise about 5% w/v to about 15% w/v of ethanol and about 10% w/v to about 25% w/v of benzyl alcohol, or about 7.5% w/v to about 12.5% w/v ethanol and about 15% w/v to about 22.5% w/v benzyl alcohol, or about 7.5% w/v to about 12.5% w/v ethanol and about 10% w/v to about 25% w/v benzyl alcohol, or about 10% w/v to about 12% w/v ethanol and about 17% w/v to about 20% w/v benzyl alcohol.

Optionally and in any embodiment, an intranasal composition, as disclosed herein, may be substantially free or free of polymeric glycols, such as polyethylene glycol, without diminishing the therapeutic benefit of the benzodiazepine administered via the intranasal composition. For example, in any embodiment, an intranasal composition, as disclosed herein, may be substantially free or free of a polymeric glycol having a molecular weight greater than about 200 g/mol. Additionally or alternatively, in any embodiment, an intranasal composition as disclosed herein may comprise very little water, substantially no water, or are completely free of water and are non-aqueous. For example, an intranasal composition may consist essentially of or consist of 1) a benzodiazepine drug; 2) one or more alkyl maltosides (e.g., DDM and/or TDM), and 3) a carrier system consisting of a) one or more natural or synthetic tocopherols or tocotrienols and b) one or more alcohols and is optionally substantially free of water.

In addition to the benzodiazepine and the carrier system described above, the intranasal compositions, as disclosed herein, comprise about 0.01% w/v to about 1% w/v of an alkyl maltoside, such as octyl-, nonyl-, decyl-, undecyl-, dodecyl, tridecyl, tetradecyl, pentadecyl, octadecyl α- or β-D-maltoside. In any embodiment, an intranasal composition may comprise one or both of dodecyl maltoside (DDM) and tetradecyl maltoside (TDM). For example, in any embodiment, an intranasal composition may comprise about 0.01% w/v to about 1% w/v of the alkyl maltoside, such as about 0.05% w/v to about 0.5% w/v, or about 0.125% w/v to about 0.5% w/v. In particular examples, an intranasal composition comprises about 0.1% w/v to about 0.5% w/v dodecyl maltoside (DDM), about 0.15% w/v to about 0.3% w/v DDM, 0.18% w/v dodecyl maltoside, or about 0.25% w/v DDM.

The toxicokinetics and metabolism of alkyl glycosides, such as Intravail A3 (dodecyl maltoside), have been studied in detail under Organization for Economic Co-operation and Development (OECD) Guidelines for Testing of Chemicals. Orally and nasally administered alkyl glycosides are hydrolyzed to glucose and the corresponding long chain alcohol. No toxic metabolites are formed at any stage in the metabolic process. Dodecyl maltoside is a component (up to approximately 25%) of a mixture of alkyl glycosides that are the subject of an application for Generally Recognized as Safe (GRAS) status designation by the US FDA Center for Food Safety and Nutrition (CF SAN) and the US Environmental Protection Agency (EPA) based on their use as detergents or surfactants as a component of compounds in food industry and agricultural usages. With their use in these contexts, there is no established limitation on the oral or topical exposure allowed for humans.

Advantageously, it has been observed that the intranasal compositions, as described herein, do not support the growth of bacteria and therefore may be substantially free or free of any antibacterial agents or other preservatives. However, the use of an antibacterial does not preclude the therapeutic benefits of administering a benzodiazepine via an intranasal composition as described herein. Therefore, in any intranasal composition as disclosed herein, one or more additional preservation, anti-degradation, antibacterial, or antifungal agents may be included. An intranasal composition, as disclosed herein, may further optionally comprise one or more agents to enhance appearance, taste, or odor.

Methods of Use

The present disclosure provides a method of treating a pediatric subject having a seizure disorder. This method involves administering, to a pediatric subject that is 2 to 5 years old, a composition comprising an effective amount of a benzodiazepine (e.g., diazepam), an alkyl maltoside, and a carrier system comprising one or more natural or synthetic tocopherols or tocotrienols and one or more alcohols, wherein said administering is to a nasal mucosal membrane of the pediatric subject to treat the seizure disorder.

Another aspect of the disclosure provides methods of treating recurrent seizures in a pediatric subject. This method involves administering, to a pediatric subject that is 2 to 5 years old, a composition comprising an effective amount of benzodiazepine (e.g., diazepam), an alkyl maltoside, and a carrier system comprising one or more natural or synthetic tocopherols or tocotrienols and one or more alcohols, wherein said administering is to a nasal mucosal membrane of the pediatric subject during or before a seizure.

Another aspect of the disclosure provides a method of preventing a seizure in a pediatric subject. This method comprises administering a composition, to a pediatric subject that is 2 to 5 years old, comprising an effective amount of benzodiazepine (e.g., diazepam), an alkyl maltoside, and a carrier system comprising one or more natural or synthetic tocopherols or tocotrienols and one or more alcohols to a nasal mucosal membrane of the pediatric subject during a prodromal or pre-ictal phase of the seizure.

In another aspect, the present disclosure provides a method of increasing the time to a second seizure in a pediatric subject suffering from recurrent seizures. This method comprises administering, to a pediatric subject that is 2 to 5 years old, a composition comprising an effective amount of benzodiazepine (e.g., diazepam), an alkyl maltoside, and a carrier system comprising one or more natural or synthetic tocopherols or tocotrienols and one or more alcohols to a nasal mucosal membrane of the pediatric subject during or before a first seizure.

The intranasal compositions comprising benzodiazepine for use in the methods described herein, comprise about 0.01% w/v to about 1% w/v of an alkyl maltoside, and a carrier system comprising about 30% w/v to about 90% w/v of a natural or synthetic tocopherol, a natural or synthetic tocotrienol, or a combination thereof, and about 10% w/v to about 70% w/v of one or more alcohols. These compositions provide therapeutic benefit to a pediatric subject when administered to the intranasal mucosal membrane of the pediatric subject. Administration of the intranasal composition may comprise spraying at least a portion of a therapeutically effective amount of a benzodiazepine via the intranasal composition into at least one nostril, such that the intranasal composition contacts the nasal mucosal membrane of the pediatric subject. In another example, administration of the intranasal composition may comprise spraying at least a portion of a therapeutically effective amount of a benzodiazepine via the intranasal composition into each nostril. In yet another example, administration of the intranasal composition may comprise spraying a first quantity of the intranasal composition into the first nostril, spraying a second quantity of the intranasal composition into a second nostril, and optionally after a pre-selected time delay, spraying a third quantity of the intranasal composition into the first nostril. Optionally after a pre-selected time delay, a fourth quantity of the intranasal composition may be administered to the second nostril.

A benzodiazepine may be administered via any intranasal composition as disclosed herein to treat a condition, disorder, syndrome, or disease for which administration of a benzodiazepine drug may provide therapeutic benefit. Non-limiting examples of benzodiazepines that may be administered via the intranasal compositions, as disclosed herein, for therapeutic benefit include alprazolam, brotizolam, chlordiazepoxide, clobazam, clonazepam, clorazepam, demoxazepam, diazepam, flumazenil, flurazepam, halazepam, olanzapine, midazolam, nordazepam, medazepam, nitrazepam, oxazepam, lorazepam, prazepam, quazepam, triazolam, temazepam, loprazolam, any pharmaceutically acceptable salt thereof, as well as any combinations thereof. The condition, disorder, syndrome, or disease may have associated therewith undesirable symptoms which may be ameliorated through the administration of a benzodiazepine. In one example, the conditions, disorder, syndrome, disease, or symptoms thereof may be treated by administering the intranasal composition at any time before or after onset of a symptom of the condition, disorder, syndrome, or disease which may be treatable with a benzodiazepine. For example, the intranasal compositions disclosed herein, comprising a benzodiazepine, may be used to treat conditions, disorders, syndromes, and diseases as well as symptoms associated therewith, such as seizures and seizure disorders, such as epilepsy.

The intranasal compositions, as disclosed herein, may be used in preventing (i.e., inhibiting the onset of a seizure) or treating a seizure or seizure disorder, condition, syndrome, or disease. Therefore, in one aspect, the present disclosure provides a method of preventing or treating a seizure in a pediatric subject in need thereof comprising administering a composition comprising: an effective amount of a benzodiazepine (such as diazepam, lorazepam, midazolam, or the like); about 0.01% w/v to about 1% w/v of an alkyl maltoside; and a carrier system comprising about 30% w/v to about 90% w/v of a natural or synthetic tocopherol, a natural or synthetic tocotrienol, or a combination thereof, and about 10% w/v to about 70% w/v of one or more alcohols, to a nasal mucosal membrane of the pediatric subject. For example, an intranasal composition, as disclosed herein, may comprise about 2.5 mg to about 20 mg of diazepam, about 0.01% w/v to about 1% w/v of an alkyl maltoside, about 55% w/v to about 70% w/v of a natural or synthetic tocopherol or tocotrienol, and a mixture of about 5% w/v to about 15% w/v benzyl alcohol and about 10% w/v to about 25% w/v ethanol. Any intranasal composition, as disclosed herein, is suitable and may be used to treat or prevent seizures, such as epileptic seizures, absence seizures, myoclonic seizures, clonic seizures, tonic seizures, tonic-clonic seizures, atonic seizures, focal seizures, atonic seizures, and combinations thereof. Seizures that may be treated with the disclosed intranasal compositions include acute seizures, acute repetitive seizures, or a seizure that is part of a seizure cluster.

The progression of a seizure event may be divided into phases. For example, a seizure event may comprise one or more of a prodromal phase, a pre-ictal phase, an ictal phase/peri-ictal phase, and a post-ictal phase. In accordance with the methods of treating or inhibiting the onset of a seizure a seizure as disclosed herein, a benzodiazepine may be administered via an intranasal composition as disclosed herein during any phase, such as the prodromal, pre-ictal, and ictal/peri-ictal, post-ictal, or interictal phase. In some embodiments, a benzodiazepine is administered via an intranasal composition as disclosed herein during a prodromal or pre-ictal phase prevent or reduce the severity or length of an impending seizure. In some embodiments, a benzodiazepine is administered via an intranasal composition as disclosed herein during the pre-ictal or ictal phase to acutely treat an active seizure. In some embodiments, for example, if the intranasal composition is unavailable during a prodromal, pre-ictal, or ictal phase, the intranasal composition may be administered during a post-ictal phase. Such an administration may serve, for example, to prevent a subsequent seizure or to reduce any lingering effects from the current seizure event.

A pediatric subject may or may not recognize a prodromal phase as a feeling or sensation, such as confusion, anxiety, irritability, headache, tremor, anger, or other mood disturbance. The prodromal phase is not generally characterized as part of an active seizure but may serve as a warning sign to the pediatric subject of an impending seizure. Thus, in any embodiment, the intranasal compositions disclosed herein may be administered during the prodromal phase to prevent a seizure from occurring or reduce the severity of the seizure. In the absence of or in addition to a pediatric subject's self-recognition of a prodromal phase, a pediatric subject may employ a monitoring device, for example, a medical device such as those available from EMPATICA™, that measures various biometric data of the pediatric subject to enable identification of an impending seizure and therefore suggest administration of an intranasal composition, as disclosed herein, prior to the start of a seizure. Therefore, in another aspect, the present disclosure provides a method of preventing a seizure, inhibiting the onset of a seizure, or reducing the severity or length of an impending seizure in a pediatric subject comprising administering a benzodiazepine during a prodromal phase via an intranasal composition comprising an effective amount of a diazepam; about 0.01% w/v to about 1% w/v of an alkyl maltoside; and a carrier system comprising about 30% w/v to about 90% w/v of a natural or synthetic tocopherol, a natural or synthetic tocotrienol, or a combination thereof, and about 10% w/v to about 70% w/v of one or more alcohols to the nasal mucosal membrane of the pediatric subject.

Pre-ictal (or early ictal) likewise may not be experienced by every pediatric subject but may include experience of aura or sensory disturbance. Examples include, but are not limited to, vision loss/blurring, flickering vision, hallucinations, ringing/buzzing sounds, strange smells, bitter/acidic taste, out-of-body sensation, nausea, numbness, tingling, dizziness, pain, twitching, strong emotions, déjàvu, or jamais vu. Therefore, in another aspect, the present disclosure provides a method of preventing or reducing the severity or length of an impending seizure in a pediatric subject comprising administering, for example, by self-administration, a benzodiazepine during a pre-ictal phase via an intranasal composition comprising an effective amount of a diazepam; about 0.01% w/v to about 1% w/v of an alkyl maltoside; and a carrier system comprising about 30% w/v to about 90% w/v of a natural or synthetic tocopherol, a natural or synthetic tocotrienol, or a combination thereof, and about 10% w/v to about 70% w/v of one or more alcohols to the nasal mucosal membrane of the pediatric subject.

An ictal/peri-ictal phase includes the time period wherein active seizure is experienced or physiologically measured and may include symptoms such as, but not limited to, confusion, memory lapse, distractedness, sense of detachment, eye or head twitching movement in one direction, inability to move or speak, loss of bladder and/or bowel control, pale/flushed skin, hearing loss, strange sounds, vision loss, blurring, flashing vision, chewing or lip-smacking, unusual physical activity, walking/running, pupil dilation, difficulty breathing, racing heart, sweating, tremors, twitching, arm or leg stiffening, numbness, or drooling. Therefore, in another aspect, the present disclosure provides a method of reducing the severity or length of an active seizure in a pediatric subject comprising administering a benzodiazepine during a an ictal or peri-ictal phase via an intranasal composition comprising an effective amount of a diazepam; about 0.01% w/v to about 1% w/v of an alkyl maltoside; and a carrier system comprising about 30% w/v to about 90% w/v of a natural or synthetic tocopherol, a natural or synthetic tocotrienol, or a combination thereof, and about 10% w/v to about 70% w/v of one or more alcohols to the nasal mucosal membrane of the pediatric subject.

After the seizure or ictal phase ends, a pediatric subject may experience a recovery or post-ictal phase which may span a minute or less or may continue for minutes, hours, or days. Typical symptoms of a post-ictal phase include, but are not limited to, drowsiness, confusion, memory loss, nausea, general malaise, body soreness, difficulty finding names/words, headaches, thirst, arm/leg weakness, hypertension, or feelings of fear, embarrassment, or sadness. The period between the post-ictal phase and the beginning of the next seizure is termed the "interictal" phase. Therefore, in another aspect, the present disclosure provides a method of preventing or reducing the severity or length of a subsequent seizure in a pediatric subject comprising administering a benzodiazepine during a post-ictal or interictal phase via an intranasal composition comprising an effective amount of a diazepam; about 0.01% w/v to about 1% w/v of an alkyl maltoside; and a carrier system comprising about 30% w/v to about 90% w/v of a natural or synthetic tocopherol, a natural or synthetic tocotrienol, or a combination thereof, and about 10% w/v to about 70% w/v of one or more alcohols to the nasal mucosal membrane of the pediatric subject.

The present disclosure also provides a method of treating a pediatric subject having Rett syndrome. This method involves administering, to a pediatric subject that is 2 to 5 years old, a composition comprising an effective amount of a benzodiazepine (e.g., diazepam), an alkyl maltoside, and a carrier system comprising one or more natural or synthetic tocopherols or tocotrienols and one or more alcohols, wherein said administering is to a nasal mucosal membrane of the pediatric subject to treat the Rett syndrome.

The present disclosure also provides a method of treating a pediatric subject having Lennox-Gastaut syndrome. This method involves administering, to a pediatric subject that is 2 to 5 years old, a composition comprising an effective amount of a benzodiazepine (e.g., diazepam), an alkyl maltoside, and a carrier system comprising one or more natural or synthetic tocopherols or tocotrienols and one or more alcohols, wherein said administering is to a nasal mucosal membrane of the pediatric subject to treat the Lennox-Gastaut syndrome.

In any embodiment, an intranasal composition can comprise an effective amount of diazepam. Effective amounts of diazepam that may be administered via the intranasal compositions, as disclosed herein, include about 2.5 mg to about 20 mg of diazepam, such as about 5 mg to about 15 mg of diazepam, about 5 mg to about 10 mg of diazepam, about 10 mg to about 20 mg of diazepam, or about 15 mg to about 20 mg. Effective dosing may, in any embodiment, be determined based on the body weight of the pediatric subject to which the diazepam will be administered. For example, for any given pediatric subject having a body weight (in kg), a dose of about 0.25 mg/kg to about 0.60 mg/kg may be administered. For example, suitable doses include about 0.27 mg/kg, about 0.35 mg/kg, about 0.40 mg/kg, about 0.50 mg/kg, or about 0.55 mg/kg of body weight may be administered to a pediatric subject. In some embodiments, a suitable dose is about 0.50 mg/kg of body weight. Diazepam may be included in a liquid composition comprising an about 0.01% w/v to about 1% w/v of an alkyl maltoside and a carrier system comprising about 30% w/v to about 90% w/v of a natural or synthetic tocopherol, a natural or synthetic tocotrienol, or a combination thereof, and about 10% w/v to about 70% w/v, the intranasal composition having a volume of about 10 μL to about 200 μL, about 50 μL to about 150 μL, about 75 μL to about 125 μL, about 75 μL, about 100 μL, or about 125 μL. For example, 5 mg, 7.5 mg, 10 mg, 15 mg, or 20 mg diazepam may be administered in a volume of about 75 μL, 100 μL, or 125 μL. A dose may be administered to a single nostril or split up between nostrils. For example, a dose of 5 mg diazepam in 100 μL, 7.5 mg diazepam in 100 μL, 10 mg diazepam in 100 μL, or 20 mg diazepam in 100 μL may be administered in a single nostril. A dose of 10 mg may alternatively be administered as a dose of 5 mg diazepam in 100 μL in each nostril. Similarly, a 15 mg dose may be administered, for example, as 7.5 mg diazepam in 100 μL to each nostril. A 20 mg dose may be administered, for example, 10 mg diazepam in 100 μL to each nostril.

In one embodiment, the intranasal composition administered in accordance with any of the methods disclosed herein comprises 5% w/v benzodiazepine, 56.5% w/v vitamin E, 0.25% DDM, 10.5% benzyl alcohol, and an amount of ethanol sufficient to reach the desired volume (e.g., 100 μL).

In one embodiment, the intranasal composition administered in accordance with any of the methods disclosed herein comprises 10% w/v benzodiazepine, 56.5% w/v vitamin E, 0.25% DDM, 10.5% benzyl alcohol, and an amount of ethanol sufficient to reach the desired volume (e.g., 100 μL).

In one embodiment, the intranasal composition administered in accordance with any of the methods disclosed herein comprises 20% w/v benzodiazepine, 56.5% w/v vitamin E, 0.25% DDM, 10.5% benzyl alcohol, and an amount of ethanol sufficient to reach the desired volume (e.g., 100 μL).

An effective amount of a benzodiazepine may be administered to a pediatric subject via an intranasal composition, as disclosed herein, multiple times, if necessary, to effectively treat or prevent a seizure. In accordance with the methods disclosed herein, the administering is carried out to reduce one or more of the frequency, length, and severity of recurrent seizures in the pediatric subject. As such, in another aspect, the present disclosure provides a method of preventing (i.e., inhibiting the onset of a seizure) or treating a seizure comprising: administering a first dose of a composition comprising an effective amount of a benzodiazepine, such as diazepam; about 0.01% w/v to about 1% w/v of an alkyl maltoside; and a carrier system comprising about 30% w/v to about 90% w/v of a natural or synthetic tocopherol, a natural or synthetic tocotrienol, or a combination thereof, and about 10% w/v to about 70% w/v of one or more alcohols to a nasal mucosal membrane of the pediatric subject during or before a seizure, wherein when adequate cessation or prevention of the seizure is not achieved within 4 hours, 2 hours, 1 hour, 30 minutes, 15 minutes, or 10 minutes after the administering of the first dose, one or more subsequent doses of the composition are administered to the pediatric subject. For example, a composition comprising about 5 mg to about 20 mg of diazepam, about 0.01% w/v to about 1% w/v of an alkyl maltoside; and a carrier system comprising about 30% w/v to about 90% w/v of a natural or synthetic tocopherol, a natural or synthetic tocotrienol, or a combination thereof and about 10% w/v to about 70% w/v of one or more alcohols may be administered in a first dose and upon inadequate cessation of the seizure, a second dose of the composition may be administered. The second dose may be identical in volume and strength as the first dose. Optionally, if adequate cessation or prevention of the seizure is not achieved within 4 hours, 2 hours, 1 hour, 30 minutes, 15 minutes, or 10 minutes after administration of the second dose, the method may further comprise administering a third dose of the composition.

Advantageously, administration of a benzodiazepine via an intranasal composition, as disclosed herein, to a pediatric subject may induce a therapeutic benefit to the pediatric subject substantially before a therapeutically relevant benzodiazepine concentration is achieved in the blood plasma of the pediatric subject. For example, maximum plasma concentrations ($C_{max}$) of about 200 ng/mL to about 500 ng/mL may be reached at a $T_{max}$ of about an hour or more, such as about 1 hour, about 1.25 hours, about 1.5 hours, or about 2 hours following administration of a benzodiazepine via an intranasal composition as described herein. As such, the PK profiles of intranasal compositions, as disclosed herein, appear similar to oral formulations (see, e.g., Friedman, et al., Clinical Pharmacology & Therapeutics, 1992; 52(2): pp. 139-150, which is incorporated in its entirety herein by reference.)

Several clinical studies with prior intranasal formulations of benzodiazepines (e.g., diazepam) have been reported in the literature. Generally, the absolute bioavailability of the benzodiazepine administered via these formulations was low (about 50%). For example, Gizurarson S. and Bechgaard E; *Diabetes Res Clin Pract.* 1991; 12(2): 71-84, which is incorporated in its entirety herein by reference, reports the administering of a 2 mg dose of a 20 mg/mL diazepam solution dissolved in 5% glycofurol in polyethylene glycol 200. Mean bioavailability of the benzodiazepine was reported to be 50.4%±23.3% with a $T_{max}$ of 18±11 minutes. Lindhardt, et al.; *Br J Clin Pharmacol.* 2001; 52(5): 521-527, which is incorporated in its entirety herein by reference, evaluated an intranasal formulation of diazepam with doses of 4 mg and 7 mg in polyethylene glycol 300 in seven healthy volunteers against a 5 mg IV dose. The benzodiazepine administered via the intranasal formulation had a relative bioavailability of 45% and 42%, a $C_{max}$ of 99 ng/mL and 170 ng/mL, and a $T_{max}$ of 18 minutes and 42 minutes for the 4 mg and 7 mg doses, respectively. Ivaturi et al.; *Acta Neurol Scand.* 2009; 120(5):353-357, which is incorporated in its entirety herein by reference, conducted a study of the bioavailability and tolerability of diazepam administered to healthy volunteers intranasally. They compared 5 mg and 10 mg intranasal diazepam doses with a 5 mg IV dose of diazepam. Following the 5 mg and 10 mg doses, the median $T_{max}$ was 20 and 30 minutes, respectively, and the mean $C_{max}$ was 134.3±62 ng/mL and 247.6±61 ng/mL. Estimated bioavailability of diazepam was 75% for both doses.

In contrast, absolute bioavailability of diazepam administered via an intranasal composition, as disclosed herein, achieves about 90% to about 110% bioavailability of intravenously administered diazepam. In some embodiments, about 92.5% to about 107.5% bioavailability of intravenously administered diazepam is achieved. In some embodiments, about 96% bioavailability of intravenously administered diazepam is achieved. In addition, the mean elimination half-life of benzodiazepine following administration of the intranasal composition described herein is significantly longer than other intranasal benzodiazepine compositions (i.e., $t_{1/2}$ of ~49 hours vs. 2-6 hours). This longer half-life provides a longer duration of action, lowering the risk of a second seizure or need for repeat dosing.

Accordingly, in some embodiments, administering a composition comprising an effective amount of diazepam, an alkyl maltoside, and a carrier system comprising one or more natural or synthetic tocopherols or tocotrienols and one or more alcohols as described herein to a nasal mucosal membrane of a pediatric subject during or before a seizure is effective to reduce clinical seizure activity in the pediatric subject for a period of at least 8 hours after said administering. In some embodiments, the clinical seizure activity is reduced for a period of at least 12 hours after said administering, a period of at least 18 hours after said administering, a period of at least 24 hours after said administering, a period of at least 36 hours after said administering, a period of at least 48 hours after said administering, or a period of >48 hours after said administering. The longer half-life and longer duration of action is particularly useful for the treatment of a pediatric subject experiencing a seizure cluster or acute repetitive seizures.

In some embodiments, administering a composition comprising an effective amount of diazepam as describe herein to a nasal mucosal membrane of a pediatric subject during or before a seizure is effective to prevent a second seizure in the pediatric subject for a period of at least 8 hours after said administering. In some embodiments, the second seizure in the pediatric subject is prevented for a period of at least 12 hours after said administering, a period of at least 18 hours after said administering, a period of at least 24 hours after said administering, a period of at least 36 hours after said administering, a period of at least 48 hours after said administering, or a period of >48 hours after said administering. The prevention of a second seizure is particularly beneficial for a pediatric subject experiencing a seizure cluster or acute repetitive seizures.

In some embodiments, administering a composition comprising an effective amount of diazepam as described herein to a nasal mucosal membrane of a pediatric subject during or before a seizure is effective to preclude the need for a second administration of the composition within 24-hours of experiencing the first seizure. In some embodiments, the dose is effective to preclude the need for a second administration of the composition within 48-hours or more of experiencing the first seizure.

Equally surprisingly is that a therapeutic benefit of the disclosed intranasal compositions is realized in a pediatric subject prior to PK-based predictions. For example, a therapeutic benefit may be realized in a pediatric subject within 10 minutes of intranasal administration of a benzodiazepine via an intranasal composition as disclosed herein, such as within 5 minutes, within 1 minute, within about 30 seconds to 4 minutes, within about 30 seconds to about 3 minutes, within about 30 seconds to about 2 minutes, or within about 30 seconds to about 1 minute after intranasal administration. Examples of therapeutic benefits that may be realized in a pediatric subject include, but are not limited to, experiencing no seizure, a less-severe seizure, or a shorter seizure as compared to a pediatric subject who is administered a benzodiazepine orally or intravenously. This is particularly surprising and advantageous, since the only non-IV administration route providing rapid effects is that which is administered rectally (e.g., DIASTAT™), and that therapeutic effect is reported to occur in about 5 minutes to about 10 minutes, which is more than twice as long as observed using the intranasal compositions as disclosed herein.

Therefore, in another aspect, the present disclosure provides a method of preventing (i.e., inhibiting the onset) or treating a seizure in a pediatric subject in need thereof and effecting a reduction in severity of the seizure within about 10 minutes after administration of an intranasal composition comprising an effective amount of a benzodiazepine, about 0.01% w/V to about 1% w/v of an alkyl maltoside (e.g., DDM or TDM), and a carrier system comprising about 30% w/v to about 90% w/v of a natural or synthetic tocopherol, a natural or synthetic tocotrienol, or a combination thereof and about 10% w/v to about 70% w/v of one or more alcohols to a nasal mucosal membrane of the pediatric subject during or before a seizure. For example, an intranasal composition may comprise an effective amount of a benzodiazepine (such as about 5 mg to about 20 mg of diazepam), about 0.01% w/v to about 1% w/v of an alkyl maltoside, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the composition comprises about 5% to about 20% w/v of diazepam, about 56.5% w/v vitamin E, about 0.25% DDM, about 10.5% benzyl alcohol, and an amount of ethanol sufficient to reach the desired volume (e.g., 100 μL). In accordance with the methods disclosed herein, the administering is carried out to reduce one or more of the frequency, length, and severity of recurrent seizures in the pediatric subject.

Quantitatively, a therapeutic effect of a benzodiazepine administered via an intranasal composition, as disclosed herein, on seizure activity can be detected by monitoring beta rhythm or beta frequency by EEG. Changes in beta frequency, after intranasal administration of 20 mg of diazepam via an intranasal composition have been observed within about 10 minutes after intranasal administration. In comparison, beta frequency after oral administration of 10 mg diazepam does not change until about 1.5 to 2 hours (see, e.g., Friedman, et al., as disclosed above). The divergence of PD and PK profiles, more particularly, the observation that the PK profile of diazepam administered according to the methods disclosed herein mimics the $T_{max}$ and $C_{max}$ of oral dosage forms but has the bioavailability and rapid onset of therapeutic benefit of a benzodiazepine administered intravenously or rectally, is surprising and unexpected. Despite similar systemic drug concentrations, therapeutic benefit evidenced in both cessation of seizure as well as a change in measurable beta frequency, is achieved more rapidly using the intranasal compositions disclosed herein than in oral dosage forms. Additionally, therapeutic benefits are realized in a timeframe similar to IV administration while avoiding the high and dangerous systemic circulation concentrations.

Therefore, in another aspect, the present disclosure provides a method of preventing (i.e., inhibiting the onset) or treating a seizure in a pediatric subject comprising modulating the beta frequency of the pediatric subject by administering a composition comprising an effective amount of a benzodiazepine (e.g., diazepam), about 0.01% w/v to about 1% w/v of an alkyl maltoside (e.g., DDM or TDM), and a carrier system comprising about 30% w/v to about 90% w/v of a natural or synthetic tocopherol, a natural or synthetic tocotrienol, or a combination thereof and about 10% w/v to about 70% w/v of one or more alcohols to a nasal mucosal membrane of the pediatric subject during or before a seizure. For example, an intranasal composition may comprise an effective amount of a benzodiazepine (such as about 5 mg to about 20 mg of diazepam), about 0.01% w/v to about 1% w/v of an alkyl maltoside, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the composition comprises about 5% to about 20% w/v of diazepam benzodiazepine, about 56.5% w/v vitamin E, about 0.25% DDM, about 10.5% benzyl alcohol, and an amount of ethanol sufficient to reach the desired volume (e.g., 100 μL). In accordance with the methods disclosed herein, the administering is carried out to reduce one or more of the frequency, length, and severity of recurrent seizures in the pediatric subject. Changes in beta frequency in a pediatric subject following administration of a benzodiazepine (e.g., diazepam) via the intranasal composition to the pediatric subject may occur within about 30 minutes, within about 25 minutes, within about 20 minutes, within about 15 minutes, within about 10 minutes, or within about 5 minutes after administration of the benzodiazepine.

The systemic presence of benzodiazepines is often accompanied by undesirable side effects such as, but not limited to, somnolence, euphoria, headache/migraine, suicidal ideation or behavior, depression, vasodilation, diarrhea, ataxia, dizziness, incoordination, rash, asthma, confusion, slurred speech, muscle weakness, memory problems, dry mouth, constipation, and blurred vision. As such, compliance by a pediatric subject with treatment regimens would be poor, as a pediatric subject wishes to avoid undesirable side effects. Additionally, a pediatric subject may delay systemic administration in an attempt to avoid the undesirable side effects.

It is expected that pediatric subjects treated with benzodiazepine via an intranasal composition, may experience lower incidence and/or a reduced severity of many of these aforementioned side effects, such as somnolence, euphoria, headache, suicidal ideation and behavior, depression, incoordination, rash, asthma, and vasodilation. Therefore, a pediatric subject undergoing treatment using the intranasal compositions, as disclosed herein, may be less likely to discontinue use or delay use of the composition to treat a seizure as compared to a pediatric subject using a benzodiazepine composition administered orally, intravenously, or rectally.

As such, in another aspect, the present disclosure provides a method of preventing (i.e., inhibiting the onset) or treating a seizure in a pediatric subject in need thereof comprising administering to the pediatric subject a composition comprising an effective amount of a benzodiazepine, about 0.01% w/v to about 1% w/v of an alkyl maltoside (e.g., DDM or TDM), and a carrier system comprising about 30% w/v to about 90% w/v of a natural or synthetic tocopherol, a natural or synthetic tocotrienol, or a combination thereof and about 10% w/v to about 70% w/v of one or more alcohols to a nasal mucosal membrane of the pediatric subject during or before a seizure, wherein the pediatric subject experiences a reduced incidence or severity of euphoria after the administering. For example, the incidence or severity of euphoria may be reduced in the pediatric subject by about 5%, about 10%, about 15%, about 20% about 25%, about 30%, about 35%, about 40%, about 45%, about 50%, or greater than 50% relative to euphoria experienced after administration of a therapeutically effective amount of diazepam via rectal, intravenous, or oral administration. For example, an intranasal composition may comprise an effective amount of a benzodiazepine (such as about 5 mg to about 20 mg of diazepam), about 0.01% w/v to about 1% w/v of an alkyl maltoside, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the composition comprises about 5% to about 20% w/v of diazepam, about 56.5% w/v vitamin E, about 0.25% DDM, about 10.5% benzyl alcohol, and an amount of ethanol sufficient to reach the desired volume (e.g., 100 μL). In accordance with the methods disclosed herein, the administering is carried out to reduce one or more of the frequency, length, and severity of recurrent seizures in the pediatric subject, and may have an added benefit of reduced euphoria thereafter.

In another aspect, the present disclosure provides a method of preventing (i.e., inhibiting the onset) or treating a seizure in a pediatric subject in need thereof comprising administering to the pediatric subject a composition comprising an effective amount of a benzodiazepine, about 0.01% w/v to about 1% w/v of an alkyl maltoside (e.g., DDM or TDM), and a carrier system comprising about 30% w/v to about 90% w/v of a natural or synthetic tocopherol, a natural or synthetic tocotrienol, or a combination thereof and about 10% w/v to about 70% w/v of one or more alcohols to a nasal mucosal membrane of the pediatric subject during or before a seizure, wherein the pediatric subject experiences a reduced incidence or severity of headache after the administering. For example, the incidence or severity of headaches may be reduced in the pediatric subject by about 5%, about 10%, about 15%, about 20% about 25%, about 30%, about 35%, about 40%, about 45%, about 50%, or greater than 50% relative to headaches experienced after administration of a therapeutically effective amount of diazepam via rectal, intravenous, or oral administration. For example, an intranasal composition, as disclosed herein, may comprise an effective amount of a benzodiazepine (such as about 5 mg to about 20 mg of diazepam), about 0.01% w/v to about 1% w/v of an alkyl maltoside, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the composition comprises about 5% to about 20% w/v of diazepam, about 56.5% w/v vitamin E, about 0.25% DDM, about 10.5% benzyl alcohol, and an amount of ethanol sufficient to reach the desired volume (e.g., 100 μL). In accordance with the methods disclosed herein, the administering is carried out to reduce one or more of the frequency, length, and severity of recurrent seizures in the pediatric subject, and may have an added benefit of reduced headache severity or length thereafter.

In another aspect, the present disclosure provides a method of preventing (i.e., inhibiting the onset) or treating a seizure in a pediatric subject in need thereof comprising administering to the pediatric subject a composition comprising an effective amount of a benzodiazepine, about 0.01% w/v to about 1% w/v of an alkyl maltoside (e.g., DDM or TDM), and a carrier system comprising about 30% w/v to about 90% w/v of a natural or synthetic tocopherol, a natural or synthetic tocotrienol, or a combination thereof and about 10% w/v to about 70% w/v of one or more alcohols to a nasal mucosal membrane of the pediatric subject during or before a seizure, wherein the pediatric subject experiences a reduced incidence or severity of suicidal thoughts, behaviors, or tendencies after the administering. For example, the incidence or severity of suicidal thought, behavior, or tendency may be reduced in the pediatric subject by about 5%, about 10%, about 15%, about 20% about 25%, about 30%, about 35%, about 40%, about 45%, about 50%, or greater than 50% relative to suicidal thought, behavior, or tendency experienced after administration of a therapeutically effective amount of diazepam via rectal, intravenous, or oral administration. For example, an intranasal composition, as disclosed herein, may comprise an effective amount of a benzodiazepine (such as about 5 mg to about 20 mg of diazepam), about 0.01% w/v to about 1% w/v of an alkyl maltoside, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the composition comprises about 5% to about 20% w/v of diazepam, about 56.5% w/v vitamin E, about 0.25% DDM, about 10.5% benzyl alcohol, and an amount of ethanol sufficient to reach the desired volume (e.g., 100 μL). In accordance with the methods disclosed herein, the administering is carried out to reduce one or more of the frequency, length, and severity of recurrent seizures in the pediatric subject, and may have an added benefit of reduced suicidal thought, behavior, or tendency thereafter.

In another aspect, the present disclosure provides a method of preventing (i.e., inhibiting the onset) or treating a seizure in a pediatric subject in need thereof comprising administering to the pediatric subject a composition comprising an effective amount of a benzodiazepine, about 0.01% w/v to about 1% w/v of an alkyl maltoside (e.g., DDM or TDM), and a carrier system comprising about 30% w/v to about 90% w/v of a natural or synthetic tocopherol, a natural or synthetic tocotrienol, or a combination thereof and about 10% w/v to about 70% w/v of one or more alcohols to a nasal mucosal membrane of the pediatric subject during or before a seizure, wherein the pediatric subject experiences a reduced incidence or severity of depression after the administering. For example, the incidence or severity of depression may be reduced in the pediatric subject by about 5%, about 10%, about 15%, about 20% about 25%, about 30%, about 35%, about 40%, about 45%, about 50%, or greater than 50% relative to depression experienced after administration of a therapeutically effective amount of diazepam via rectal, intravenous, or oral administration. For example, an intranasal composition, as disclosed herein, may comprise an effective amount of a benzodiazepine (such as about 5 mg to about 20 mg of diazepam), about 0.01% w/v to about 1% w/v of an alkyl maltoside, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the composition comprises about 5% to about 20% w/v of diazepam, about 56.5% w/v vitamin E, about 0.25% DDM, about 10.5% benzyl alcohol, and an amount of ethanol sufficient to reach the desired volume (e.g., 100 μL). In accordance with the methods disclosed herein, the administering is carried out to reduce one or more of the frequency, length, and severity of recurrent seizures in the pediatric subject, and may have an added benefit of reduced depression thereafter.

In another aspect, the present disclosure provides a method of preventing (i.e., inhibiting the onset) or treating a seizure in a pediatric subject in need thereof comprising administering to the pediatric subject a composition comprising an effective amount of a benzodiazepine, about 0.01% w/v to about 1% w/v of an alkyl maltoside (e.g., DDM or TDM), and a carrier system comprising about 30% w/v to about 90% w/v of a natural or synthetic tocopherol, a natural or synthetic tocotrienol, or a combination thereof and about 10% w/v to about 70% w/v of one or more alcohols to a nasal mucosal membrane of the pediatric subject during or before a seizure, wherein the pediatric subject experiences a reduced incidence or severity of somnolence after the administering. For example, the incidence or severity of somnolence may be reduced in the pediatric subject by about 5%, about 10%, about 15%, about 20% about 25%, about 30%, about 35%, about 40%, about 45%, about 50%, or greater than 50% relative to somnolence experienced after administration of a therapeutically effective amount of diazepam via rectal, intravenous, or oral administration. For example, an intranasal composition, as disclosed herein, may comprise an effective amount of a benzodiazepine (such as about 5 mg to about 20 mg of diazepam), about 0.01% w/v to about 1% w/v of an alkyl maltoside, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the composition comprises about 5% to about 20% w/v of diazepam, about 56.5% w/v vitamin E, about 0.25% DDM, about 10.5% benzyl alcohol, and an amount of ethanol sufficient to reach the desired volume (e.g., 100 μL). In accordance with the methods disclosed herein, the administering is carried out to reduce one or more of the frequency, length, and severity of recurrent seizures in the pediatric subject, and may have an added benefit of reduced somnolence thereafter.

Having reduced incidence of adverse effects, compliance of a treatment regimen using the compositions disclosed herein by a pediatric subject may be more complete when compared to treatment regimen using an alternate benzodiazepine composition. Therefore, in another aspect, the present disclosure provides a method of improving patient compliance with a prescribed treatment regimen for preventing (i.e., inhibiting the onset) or treating a seizure, wherein the treatment method comprises intranasally administering a composition comprising an effective amount of a benzodiazepine, about 0.01% w/v to about 1% w/v of an alkyl maltoside (e.g., DDM or TDM), and a carrier system comprising about 30% w/v to about 90% w/v of a natural or synthetic tocopherol, a natural or synthetic tocotrienol, or a combination thereof and about 10% w/v to about 70% w/v of one or more alcohols to a nasal mucosal membrane of the pediatric subject during or before a seizure. For example, an intranasal composition, as disclosed herein, may comprise an effective amount of a benzodiazepine (such as about 5 mg to about 20 mg of diazepam), about 0.01% w/v to about 1% w/v of an alkyl maltoside, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the composition comprises about 5% to about 20% w/v of diazepam, about 56.5% w/v vitamin E, about 0.25% DDM, about 10.5% benzyl alcohol, and an amount of ethanol sufficient to reach the desired volume (e.g., 100 μL). In accordance with this aspect of the disclosure, the administering is carried out to reduce one or more of the frequency, length, and severity of the recurrent seizure in the pediatric subject.

Compliance with a prescribed treatment regimen is important in effectively treating recurrent seizures in a pediatric subject. Recurrent seizures, such as those that occur in epilepsy syndromes, that are left under-treated, mistreated, or not treated may, after repetitive seizure episodes, result in neurological damage. For example, evidence of progressive damage in temporal lobe epilepsy associated with hippocampal sclerosis (TLE-HS) has been identified through neuroimaging and electroencephalography (see, e.g., Coan, A. C., and Cendes, F.; *Epilepsy & Behavior*; March 2013, 26(3): pages 313-321, which is incorporated herein in its entirety by reference). Pathologically, excessive neuronal excitability characterizing a seizure results in massive depolarization of neurons, excessive glutamate release, and increased intracellular calcium which causes a cascade of changes that ultimately result in cell death (see, e.g., Holmes, G. L.; *Neurology*; Nov. 12, 2002, 59 (9 Suppl. 5), which is incorporated in its entirety herein by reference). The deleterious effects of recurrent seizures may be evidenced, for example, by an increase in cognitive dysfunction, an increase in severity, length, or frequency of seizures. However, administration of a benzodiazepine via the intranasal compositions as disclosed herein, advantageously, result in slowed or halted cognitive decline and/or decreased severity, length, or frequency of recurrent seizures when compared to the severity, length, and frequency of recurrent seizures in a pediatric subject left un-treated or treated via a different administration route.

Thus, in another aspect, the present disclosure provides a method of treating recurrent seizures in a pediatric subject comprising administering to a pediatric subject in need thereof a composition comprising an effective amount of a benzodiazepine, about 0.01% w/v to about 1% w/v of an alkyl maltoside (e.g., DDM or TDM), and a carrier system comprising about 30% w/v to about 90% w/v of a natural or synthetic tocopherol, a natural or synthetic tocotrienol, or a combination thereof and about 10% w/v to about 70% w/v of one or more alcohols to a nasal mucosal membrane of the pediatric subject during or before a seizure. For example, an intranasal composition, as disclosed herein, may comprise about 5 mg to about 20 mg of diazepam, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the composition comprises about 5% to about 20% w/v of diazepam, about 56.5% w/v vitamin E, about 0.25% DDM, about 10.5% benzyl alcohol, and an amount of ethanol sufficient to reach the desired volume (e.g., 100 μL). In accordance with the methods disclosed herein, the administering is carried out to reduce one or more of the frequency, length, and severity of recurrent seizures in the pediatric subject.

Administering a benzodiazepine via an intranasal composition, as disclosed herein, to a pediatric subject may, in any embodiment, reduce neuronal loss caused by the recurrent seizures in a pediatric subject that would otherwise occur in the pediatric subject absent treatment or being treated with another benzodiazepine dosage form. For example, a 1% reduction, 2% reduction, 3% reduction, 4% reduction, 5% reduction, 6% reduction, 7% reduction, 8% reduction, 9% reduction, 10% reduction, 11% reduction, 12% reduction, 13% reduction, 14% reduction, 15% reduction, 16% reduction, 17% reduction, 18% reduction, 19% reduction, or a reduction greater than 20% in neuronal loss is observed in the pediatric subject following administration of a benzodiazepine via an intranasal composition, as disclosed herein, as compared to the neuronal loss that would otherwise occur absent treatment or being treated with another benzodiazepine dosage form.

Administering a benzodiazepine via an intranasal composition, as disclosed herein, for the treatment of recurrent seizures may, in any embodiment, reduce or prevent cognitive dysfunction caused by the recurrent seizures in a pediatric subject that would otherwise occur in the pediatric subject absent treatment or being treated with another benzodiazepine dosage form. In any embodiment, a 1% reduction, 2% reduction, 3% reduction, 4% reduction, 5% reduction, 6% reduction, 7% reduction, 8% reduction, 9% reduction, 10% reduction, 11% reduction, 12% reduction, 13% reduction, 14% reduction, 15% reduction, 16% reduction, 17% reduction, 18% reduction, 19% reduction, or a reduction greater than 20% in cognitive dysfunction is observed in the pediatric subject following administration of a benzodiazepine via an intranasal composition, as disclosed herein, as compared to cognitive dysfunction that would otherwise occur in the pediatric subject absent treatment or being treated with another benzodiazepine dosage form.

Dosage forms of benzodiazepines currently available have associated with them a variety of contraindications due in part to the various adverse side effects that have been observed with the administration of the dosage forms. For example, the administration of diazepam is contraindicated in pediatric subjects with glaucoma (especially acute narrow-angle glaucoma and untreated open-angle glaucoma) due to the possibility of increased intraocular pressure. With the reduced incidence of adverse side effects, the intranasal compositions disclosed herein can be safely and effectively administered to pediatric subjects with glaucoma to treat a co-morbid seizure or seizure disorder or syndrome. Accordingly, in another aspect, the present disclosure provides a method of treating or preventing (i.e., inhibiting the onset) a seizure in a pediatric subject having glaucoma, the method comprising administering to the pediatric subject a composition comprising an effective amount of a benzodiazepine, about 0.01% w/v to about 1% w/v of an alkyl maltoside (e.g., DDM or TDM), and a carrier system comprising about 30% w/v to about 90% w/v of a natural or synthetic tocopherol, a natural or synthetic tocotrienol, or a combination thereof and about 10% w/v to about 70% w/v of one or more alcohols to a nasal mucosal membrane of the pediatric subject during or before a seizure. For example, an intranasal composition, as disclosed herein, may comprise about 5 mg to about 20 mg of diazepam, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the composition comprises about 5% to about 20% w/v of diazepam, about 56.5% w/v vitamin E, about 0.25% DDM, about 10.5% benzyl alcohol, and an amount of ethanol sufficient to reach the desired volume (e.g., 100 μL). In some embodiments, the pediatric subject has narrow angle glaucoma.

Co-administration of benzodiazepines with opioids is also contraindicated as both drugs sedate users and suppress breathing, leading to a higher risk for overdose and death due to respiratory distress. With the reduced incidence of adverse side effects, the intranasal compositions disclosed herein can, in some instances, be safely and effectively administered to pediatric subjects undergoing treatment involving opioid administration. Accordingly, in another aspect, the present disclosure provides a method of treating or preventing (i.e., inhibiting the onset) a seizure in a pediatric subject taking prescription opioids, the method comprising administering a composition comprising an effective amount of a benzodiazepine, about 0.01% w/v to about 1% w/v of an alkyl maltoside (e.g., DDM or TDM), and a carrier system comprising about 30% w/v to about 90% w/v of a natural or synthetic tocopherol, a natural or synthetic tocotrienol, or a combination thereof and about 10% w/v to about 70% w/v of one or more alcohols to a nasal mucosal membrane of the pediatric subject during or before a seizure. For example, an intranasal composition, as disclosed herein, may comprise about 5 mg to about 20 mg of diazepam, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the composition comprises about 5% to about 20% w/v of diazepam, about 56.5% w/v vitamin E, 0.25% DDM, about 10.5% benzyl alcohol, and an amount of ethanol sufficient to reach the desired volume (e.g., 100 μL).

Chronic administration of benzodiazepines to treat seizures (e.g., administration of benzodiazepines more than five times per month), is also contraindicated in oral, intravenous, and rectal formulations of benzodiazepines due to the propensity to develop tolerance and/or dependence with the repeated systemic exposure to the benzodiazepine. Advantageously, the intranasal compositions disclosed herein do not induce tolerance or dependence within a pediatric subject, even when administered chronically to treat recurrent seizures, such as at least 6 times a month, more than 10 times a month, or more than 15 times a month. Therefore, the intranasal compositions disclosed herein may be used to prevent or acutely treat a seizure without regard to prior administrations and the timing thereof.

Therefore, in another aspect, the present disclosure provides a method of preventing (i.e., inhibiting the onset) or treating a seizure within a series of recurrent seizures, the method comprising administering a composition comprising an effective amount of a benzodiazepine, about 0.01% w/v to about 1% w/v of an alkyl maltoside (e.g., DDM or TDM), and a carrier system comprising about 30% w/v to about 90% w/v of a natural or synthetic tocopherol, a natural or synthetic tocotrienol, or a combination thereof and about 10% w/v to about 70% w/v of one or more alcohols to a nasal mucosal membrane of the pediatric subject during or before each of the recurrent seizures, wherein 6, 7, 8, 9, 10, 11, 12, 13, 14, 15, 16, 17, 18, 19, or more seizures occur per month. For example, an intranasal composition, as disclosed herein, may comprise about 5 mg to about 20 mg of diazepam, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the composition comprises about 5% to about 20% w/v of diazepam, about 56.5% w/v vitamin E, about 0.25% DDM, about 10.5% benzyl alcohol, and an amount of ethanol sufficient to reach the desired volume (e.g., 100 In accordance with the methods disclosed herein, the administering is carried out to reduce one or more of the frequency, length, and severity of recurrent seizures in the pediatric subject.

Administration of benzodiazepines via oral, intravenous, or rectal routes is also contraindicated in children aged 2-5 due to the potential of developing tolerance and dependence. Therefore, in addition to being suitability for pediatric subjects ages 6 and above, the compositions disclosed herein are suitable for administration in younger patient populations, such as 2-5 year olds. Therefore, in another aspect, the present disclosure provides a method of preventing (i.e., inhibiting the onset) or treating a seizure in a pediatric subject that is 2 years old, 3 years old, 4 years old, 5 years old, or older wherein the treatment method comprises administering a composition comprising an effective amount of a benzodiazepine, about 0.01% w/v to about 1% w/v of an alkyl maltoside (e.g., DDM or TDM), and a carrier system comprising about 30% w/v to about 90% w/v of a natural or synthetic tocopherol, a natural or synthetic tocotrienol, or a combination thereof and about 10% w/v to about 70% w/v of one or more alcohols to a nasal mucosal membrane of the pediatric subject during or before a seizure. For example, an intranasal composition, as disclosed herein, may comprise about 5 mg to about 20 mg of diazepam, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the composition comprises about 5% to about 20% w/v of diazepam, about 56.5% w/v vitamin E, about 0.25% DDM, about 10.5% benzyl alcohol, and an amount of ethanol sufficient to reach the desired volume (e.g., 100 In accordance with the methods disclosed herein, the administering is carried out to reduce one or more of the frequency, length, and severity of recurrent seizures in the pediatric subject.

Compared to other routes of administration, such as oral, intravenous, or rectal, the compositions disclosed herein may be administered in a much simpler manner through a nasal spray. Therefore, the pediatric subject themselves, particularly if in a prodromal or pre-ictal phase of a seizure, can effectively self-administer any intranasal composition, as disclosed herein, to their nasal mucosal membrane. Additionally, a caregiver need not be a trained medical professional to effectively administer the composition to the pediatric subject, as required, for example, in intravenous administration. Therefore, advantageously, the compositions disclosed herein provide an easily administrable dosage form that may be administered before or during a seizure for rapid and quick prevention or treatment of the seizure that has the capacity, in some instances, to provide long-term benefits.

Therapeutic Systems

Another aspect of the disclosure relates to a therapeutic system for the treatment of a seizure condition, disorder, syndrome, or disease. This therapeutic system comprises a neurological monitoring device and an intranasal benzodiazepine composition as described herein. The neurological monitoring device may comprise a smart watch (e.g., Embrace by EMPATICA™, Inc.), an adhesive sensor applied externally to the skin (e.g., the BioStamp by MC10), an implantable detecting device, an electrode patch (e.g., SPEAC System by Brain Sentinel), or any other sensing device suitable for detecting changes in neurological or other physiological parameters indicative of an impending seizure. Alternatively, and/or in addition to the monitoring device, an algorithm for predicting the onset of a seizure effect can also be employed or included in this therapeutic system (see e.g., Dauod and Bayoumi, "Efficient Epileptic Seizure Prediction Based on Deep Learing," *IEEE Trans. Biomed. Circuits Systems* 13(5): 804 (2019), which is hereby incorporated by reference in its entirety).

In accordance with this aspect of the disclosure, the intranasal benzodiazepine composition of the system comprises about 5 mg to about 20 mg of diazepam, about 55% w/v to about 70% w/v of a natural or synthetic tocopherol or tocotrienol, and a mixture of about 5% w/v to about 15% w/v benzyl alcohol and about 10% w/v to about 25% w/v ethanol. In some embodiments, the intranasal benzodiazepine composition comprises about 5%, about 10%, or about 20% w/v benzodiazepine, about 56.5% w/v vitamin E, about 0.25% DDM, about 10.5% benzyl alcohol, and an amount of ethanol sufficient to reach the desired volume (e.g., 100 μL).

The therapeutic system herein comprises a suitable therapeutic regimen for treating a seizure condition, disorder, syndrome, or disease. Pairing the monitoring device with the intranasal benzodiazepine composition described herein allows for a pediatric subject suffering a seizure condition, disorder, syndrome, or disease to recognize the onset or impending onset of seizure and administer the intranasal benzodiazepine composition prior to or at the onset of the seizure to inhibit the onset of the seizure or reduce the frequency, length, and/or severity of the seizure.

The therapeutic system described herein is also suitable to employ in a method of preventing injuries that result from seizures, e.g., falls, and preventing ongoing or further injury to the brain in recurrent seizure syndromes. In some embodiments, the therapeutic system described herein is employed as a replacement or adjuvant therapy to chronic anti-epileptic drugs to reduce or avoid associate long-term side effects of those drugs.

FURTHER EMBODIMENTS

Provided herein is an embodiment A, a method of treating a pediatric subject having a seizure disorder, said method comprising: administering, to a pediatric subject that is 2 to 5 years old, a composition comprising: an effective amount of diazepam, an alkyl maltoside, and a carrier system comprising one or more natural or synthetic tocopherols or tocotrienols and one or more alcohols, wherein said administering is to a nasal mucosal membrane of the pediatric subject to treat the seizure disorder in the pediatric subject.

In an embodiment B, the method of embodiment A wherein the effective amount of diazepam is about 2 mg to about 20 mg diazepam in a volume of about 10 μL to 200 μL of the composition.

In an embodiment C, the method of embodiment B, wherein the effective amount of diazepam is about 5 mg to about 15 mg in a volume of 100 μL to 200 μL of the composition.

In an embodiment D, the method of any one of embodiments A to C, wherein the composition is provided in a pre-primed single use dosage device containing about 100 μL of the composition.

In an embodiment E, the method of any one of embodiments A to D, wherein said administering comprises delivering about 5 mg to about 10 mg of diazepam in a volume of about 100 μL of the composition to a single nostril of the pediatric subject.

In an embodiment F, the method of any one of embodiments A to D, wherein said administering comprises delivering about 7.5 mg diazepam in a volume of 100 μL of the composition to each nostril of the pediatric subject.

In an embodiment G, the method of any one of embodiments A to F, wherein the alkyl maltoside is selected from dodecyl maltoside, tetradecyl maltoside, or a combination thereof.

In an embodiment H, the method of any one of embodiments A to G, wherein the composition comprises about 0.1% w/v to about 1% w/v of the alkyl maltoside.

In an embodiment I, the method of any one of embodiments A to H, wherein the one or more alcohols comprises a mixture of ethanol and benzyl alcohol.

In an embodiment J, the method of any one of embodiments A to I, wherein the composition comprises about 17% w/v to about 20% w/v ethanol and about 10% w/v to about 12% w/v benzyl alcohol.

In an embodiment K, the method of any one of embodiments A to J, wherein said administering reduces clinical seizure activity in the pediatric subject for a period of at least 8 hours after said administering.

In an embodiment L, the method of any one of embodiments A to J, wherein said administering reduces clinical seizure activity in the pediatric subject for a period of at least 24 hours after said administering.

In an embodiment M, the method of any one of embodiments A to J, wherein said administering reduces clinical seizure activity in the pediatric subject for a period of at least 48 hours after said administering.

In an embodiment N, the method of any one of embodiments A to J, wherein said administering prevents a second seizure in the pediatric subject for a period of at least 8 hours after said administering.

In an embodiment 0, the method of any one of embodiments A to J, wherein said administering prevents a second seizure in the pediatric subject for a period of at least 24 hours after said administering.

In an embodiment P, the method of any one of embodiments A to J, wherein said administering prevents a second seizure in the pediatric subject for a period of at least 48 hours after said administering.

In an embodiment Q, the method of any one of embodiments A to P, wherein the pediatric subject does not require a second administration of said composition within at least 24-hours of experiencing a first seizure.

In an embodiment R, the method of any one of embodiments A to Q, wherein the pediatric subject has epilepsy or an epileptic disorder.

In an embodiment S, the method of any one of embodiments A to R, wherein the administering is performed by a caregiver.

In an embodiment T, the method of any one of embodiments A to S, wherein the administering is performed in a prodromal phase or pre-ictal phase of a seizure.

In an embodiment U, the method of any one of embodiments A to S wherein the administering is performed in an ictal phase of a seizure.

In an embodiment V, the method of any one of embodiments A to U, wherein said administering achieves about 90% to about 110% bioavailability of intravenously administered diazepam.

Provided herein is an embodiment W, a method of treating recurrent seizures in a pediatric subject in need thereof, said method comprising: administering, to a pediatric subject that is 2 to 5 years old, a composition comprising: an effective amount of diazepam, an alkyl maltoside, and a carrier system comprising one or more natural or synthetic tocopherols or tocotrienols and one or more alcohols, wherein said administering is to a nasal mucosal membrane of the pediatric subject during or before a seizure.

In an embodiment X, the method of embodiment W, wherein the recurrent seizures are seizure clusters.

In an embodiment Y, the method of embodiment W, wherein the recurrent seizures are acute repetitive seizures.

In an embodiment Z, the method of embodiments W to Y, wherein the effective amount of diazepam is about 2 mg to about 20 mg diazepam in a volume of about 10 μL to 200 μL of the composition.

In an embodiment AA, the method of embodiments Z, wherein the effective amount of diazepam is about 5 mg to about 15 mg in a volume of 100 μL to 200 μL of the composition.

In an embodiment BB, the method of embodiments W to AA, wherein the composition is provided in a pre-primed single use dosage device containing about 100 μL of the composition.

In an embodiment CC, the method of embodiments W to BB, wherein said administering comprises delivering about 5 mg to about 10 mg of diazepam in a volume of about 100 μL of the composition to a single nostril of the pediatric subject.

In an embodiment DD, the method of embodiments W to CC, wherein said administering comprises delivering about 7.5 mg diazepam in a volume of 100 μL of the composition to each nostril of the pediatric subject.

In an embodiment EE, the method of embodiments W to DD, wherein the alkyl maltoside is selected from dodecyl maltoside, tetradecyl maltoside, or a combination thereof.

In an embodiment FF, the method of embodiments W to EE, wherein the composition comprises about 0.1% w/v to about 1% w/v of the alkyl maltoside.

In an embodiment GG, the method of embodiments W to FF, wherein the one or more alcohols comprises a mixture of ethanol and benzyl alcohol.

In an embodiment HH, the method of embodiments W to GG, wherein the composition comprises about 17% w/v to about 20% w/v ethanol and about 10% w/v to about 12% w/v benzyl alcohol.

In an embodiment II, the method of embodiments W to HH, wherein said administering reduces clinical seizure activity in the pediatric subject for a period of at least 8 hours after said administering.

In an embodiment JJ, the method of embodiments W to HH, wherein said administering reduces clinical seizure activity in the pediatric subject for a period of at least 24 hours after said administering.

In an embodiment KK, the method of embodiments W to HH, wherein said administering reduces clinical seizure activity in the pediatric subject for a period of at least 48 hours after said administering.

In an embodiment LL, the method of embodiments W to HH, wherein said administering prevents a second seizure in the pediatric subject for a period of at least 8 hours after said administering.

In an embodiment MM, the method of embodiments W to HH, wherein said administering prevents a second seizure in the pediatric subject for a period of at least 24 hours after said administering.

In an embodiment NN, the method of embodiments W to HH, wherein said administering prevents a second seizure in the pediatric subject for a period of at least 48 hours after said administering.

In an embodiment OO, the method of embodiments W to NN, wherein the pediatric subject does not require a second administration of said composition within at least 24-hours of experiencing a first seizure.

In an embodiment PP, the method of embodiments W to OO, wherein the pediatric subject has epilepsy or an epileptic disorder.

In an embodiment QQ, the method of embodiments W to PP, wherein the administering is performed by a caregiver.

In an embodiment RR, the method of embodiments W to QQ, wherein the administering is performed in a prodromal phase or pre-ictal phase of a seizure.

In an embodiment SS, the method of embodiments W to RR, wherein the administering is performed in an ictal phase of a seizure.

In an embodiment TT, the method of embodiments W to SS, wherein said administering achieves about 90% to about 110% bioavailability of intravenously administered diazepam.

EXAMPLES

The examples below are intended to exemplify the practice of embodiments of the disclosure but are by no means intended to limit the scope thereof.

Example 1: Formulations

Various non-limiting examples of intranasal compositions comprising a benzodiazepine, as described herein, are provided in Table 1 below. In any embodiment, the alkyl maltoside may be tetradecyl maltoside or dodecyl maltoside, preferably dodecyl maltoside. In any embodiment, the Vitamin E may be, for example, α-tocopherol, β-tocopherol, γ-tocopherol, δ-tocopherol, α-tocotrienol, β-tocotrienol, γ-tocotrienol, δ-tocotrienol, tocophersolan, preferably α-tocopherol.

TABLE 1

| | Solution No. | | | | |
|---|---|---|---|---|---|
| Component | 1 | 3 | 4 | 6 | 7 |
| diazepam (% w/v) | 5-15 | 9-11 | 10 | 5 | 7 |
| alkyl maltoside (% w/v) | 0.01-1 | 0.1-0.5 | 0.15-0.3 | 0.01-1 | 0.01-1 |
| vitamin E (% w/v) | 45-65 | 50-60 | 50-60 | 70 | 65 |
| ethanol (% w/v) | 10-25 | 15-22.5 | 17-20 | q.s. | q.s. |
| benzyl alcohol (% w/v) | 5-15 | 7.5-12.5 | 10-12 | — | — |

Example 2: An Open-Label, Single-Dose, Pharmacokinetics Study of VALTOCO® with Open-Label Safety Period in Pediatric Patients with Epilepsy The purpose of this study is to assess the pharmacokinetics (PK) of diazepam after a single intranasal dose of diazepam (VALTOCO®) administered to patients with epilepsy 2-5 years of age. Approximately 30 subjects age 2 to 5 years are to be enrolled (approximately 15 subjects between age 4 to 5 years; followed by approximately 15 subjects between age 2 to 3 years)

The primary objective of this study is to assess the PK of diazepam after a single intranasal dose of VALTOCO administered to patients with epilepsy 2-5 years of age. The primary PK variables to determine bioavailability are the maximum plasma concentration ($C_{max}$) and the area under the curve through 6 hours ($AUC_{(0-6)}$). Safety and tolerability of diazepam after intranasal administration of diazepam (VALTOCO®) in the subject population and long-term safety and tolerability of diazepam (VALTOCO®) after repeated exposure of intranasal administration of diazepam in the subject population will also be assessed.

A single dose of intranasal diazepam (VALTOCO®) is administered at either 5 mg, 10 mg or 15 mg dose based on the subject's body weight in a clinical setting followed by PK sampling. The VALTOCO® formulation contains 0.25% dodecyl maltoside (0.025 mg/100 μL).

All doses are administered by a trained medical professional as per the Instructions for Use consistent with diazepam (VALTOCO®) prescribing information. Appropriate entertainment is allowed to help the subject remain relaxed and distracted during study procedures. The study consists of a screening period, a baseline period, a single-dose period, an open-label safety period, and a follow-up phone call.

Each subject is assigned a screening number at the time of enrollment. After screening, the system automatically assigns to each qualified subject a randomization number, and a block-permutated random sequence determines which one of the following sequences for blood collection is used. A total of six (6) blood samples for PK evaluation will be collected from each subject at specific times depending on sequence:

Sequence 1: Pre-dose, 60, 120, 180, 240, and 360 min. time points

Sequence 2: Pre-dose, 15, 75, 195, 300, and 360 min. time points

Sequence 3: Pre-dose, 45, 90, 150, 210, and 360 min. time points

A range of ±5 minutes will be allowed for time points from 15 to 60 minutes and ±10 minutes for time points from 75 to 360 minutes. For all blood samples the actual time of collection will be recorded and entered into the case report form (CRF).

An initial group of approximately 15 children age 4 to 5 years are enrolled. After an initial evaluation of safety and PK in the 4 to 5 years old group, an additional group of approximately 15 subjects are enrolled in the 2 to 3 years old group.

Subjects who discontinue for any reason prior to dosing and/or obtaining at least 120 minutes of blood samples for PK assessment may be replaced at the discretion of the Sponsor. If a subject discontinues after dosing but prior to completing the PK assessment and is not evaluable, they are able to continue on in the open-label safety portion of the study.

If the subject experiences a seizure after dosing (during the blood sampling period), PK blood draws are suspended as long as required for the subject's medical care and resume when clinically feasible, provided that the subject is not treated with any other diazepam containing product. If the subject experiences a seizure after dosing and is administered an exclusionary medication (such as intravenous [IV], oral or rectal diazepam), PK blood draws are stopped, time of dosing diazepam is recorded, and the Sponsor is notified. All other safety procedures are performed as per the protocol Schedule of Study Procedures.

Subjects are discharged after the 6-hour post-dose assessments are complete provided that there are no clinically meaningful signs of sedation. For the open-label safety portion of this study, subjects are supplied with intranasal diazepam (VALTOCO®) to use as rescue medication as needed for the frequent breakthrough seizures or acute repetitive seizures (ARS) (as per VALTOCO® prescribing information). Subjects and caregivers are provided an electronic diary to record any usage of VALTOCO® for seizures including the date of use, time of seizure onset, time of dosing, time of seizure resolution, any adverse events (AEs) and any dosage or device errors.

Subjects return to the site on Day 30 (±4 day) for safety evaluations and to be provided with additional supply of study medication, and on Day 90 and Day 180 (±4 days) for safety evaluations. A phone call is conducted on Day 60, Day 120 and Day 150 (±4 days) to determine if any AEs have occurred and to follow-up on any ongoing AEs. Seven days (+4 days) after the Day 180 visit, a follow-up phone call is conducted to determine if any AEs have occurred and to follow-up on any AEs ongoing since last communication with the subject.

Safety assessments include AEs, physical examination, neurological examination, and nasal irritation assessment.

Site personnel are trained in the conduct of nasal irritation assessments based on a standardized scale.

Inclusion criteria for the study includes:

- Male or female subjects between the ages of 2 and 5 years, inclusive at time of enrollment.
- Written informed consent by legal guardian to participate in the study.
- Subject has a clinical diagnosis of epilepsy and, in the opinion of the Investigator, may need benzodiazepine intervention for seizure control.
- Subjects having either partial or generalized epilepsy with motor seizures or seizures with clear alteration of awareness, for which rescue medications are used at least once per month for the last 3 months.
- No clinically significant abnormal findings in the medical history, on the physical examination, electrocardiogram (ECG) (corrected QT interval [QTcF] less than 440 msec), or in clinical laboratory results during screening.
- Caregivers must agree to comply with all required study procedures.

Exclusion criteria for the study includes:

- A body weight is of less than 6 kg or more than 33 kg at time of enrollment.
- Subject is undergoing intracranial electroencephalogram (EEG) monitoring.
- A history of clinically significant gastrointestinal, renal, hepatic, neurologic, hematologic, endocrine, oncologic, pulmonary, immunologic, psychiatric, or cardiovascular disease, severe seasonal or non-seasonal allergies, nasal polyps or any nasal passage abnormality that could interfere with nasal spray administration, or any other condition which, in the opinion of the Investigator, would jeopardize the safety of the subject or impact the validity of the study results.
- Significant traumatic injury, major surgery or open biopsy within 30 days prior to study screening.
- Donation of blood or plasma within 30 days of the first dose of study drug.
- Participation in a clinical trial within 30 days prior to the first dose of study drug. Participation in an observational (non-interventional) study is not excluded as long as there are no scheduling conflicts with this study.
- Inadequate or difficult venous access that may jeopardize the quality or timing of the PK samples.
- Treatment with phenobarbital or primidone within 30 days of the anticipated dosing visit (i.e., baseline).
- Treatment with warfarin or dabigatran or other blood thinners within 30 days of the anticipated dosing visit (i.e., baseline).
- Treatment with any diazepam containing products within 14 days of the anticipated dosing visit (i.e., baseline).
- Use of nasal decongestants or nasal steroids within 7 days prior to the screening visit or during the study.

Treatment with any known strong or moderate inhibitors or inducers of metabolizing enzymes (e.g., CYP-P450 enzymes or MAO), including herbal medicines, within fourteen (14) days prior to the first dose of VALTOCO®, or during the study, is prohibited without approval from the Medical Monitor.

The Investigator or designee performs a complete physical and neurological examination, including head, ears, eyes, nose, and throat (HEENT), at screening and a targeted physical examination at baseline, discharge from the Clinical Research Site or equivalent (i.e., EMU), and at the Day 30, Day 90, and Day 180 visits. Results are recorded on the appropriate page of the CRF.

A medical history is obtained at screening. Medical history includes demographic data (age, sex, race/ethnicity, etc.). In addition, seizure history is obtained. The number of rescue medications used per month for the previous three (3) months is reported on the CRF. The average number of seizures over the last three (3) months are used as the baseline use. ECGs are assessed by the Investigator or a cardiologist, and a comparison to baseline ECGs is performed. The ECG report is reviewed, signed, and dated by the Investigator or cardiologist. One duplicate copy of the ECG tracing and the evaluation report are printed and sent to the Sponsor after de-identifying the subject for inclusion with the CRF. The original ECG results are kept on file at the site as source documentation.

Height are measured in centimeters at screening, baseline and the Day 30, Day 90, and Day 180 visits. Body weight is measured in kilograms at screening, baseline and the Day 30, Day 90, and Day 180 visits. Height and weight are recorded on the CRF.

A standard supine (after resting for at least 5 minutes) 12-lead ECG is performed in triplicate by a trained technician at screening and baseline.

Vital signs (temperature, pulse, and blood pressure) are obtained at screening, baseline (just prior to dosing), and at 30 (±5 min) minutes, 1 (±10 min), 2 (±15 min), 4 (±30 min), and 6 (±30 min) hours post dose, upon discharge from the Clinical Research Site or equivalent (i.e., EMU), and at the Day 30, Day 90, and Day 180 visits. Vital signs are recorded on the CRF.

The presence of HIV antibody, hepatitis B surface antigen (HbSAg), and Hepatitis C antibody is also assessed at screening.

Dosing of intranasal diazepam (VALTOCO®) are selected according to the subject's weight (rounded to the nearest kg, 0.5 mg/kg based on DIASTAT® label) based on the following:

- 6 kg to 11 kg body weight receive a 5 mg dose (50 mg/mL, 100 μL) administered as one spray in the left nostril.
- 12 kg to 22 kg body weight receive a 10 mg dose (100 mg/mL, 100 μL) administered as one spray in the left nostril.
- 23 kg to 33 kg body weight receive a 15 mg dose (75 mg/mL, 2×100 μL) administered as two 7.5 mg sprays with one spray in each nostril (the left nostril is sprayed first followed by the right nostril).

Incidences of AEs are documented and reviewed to evaluate the safety and tolerability of diazepam nasal solution. Other safety assessments include physical and neurological examination in head, ears, eyes, nose, and throat (HEENT), vital signs, laboratories (hematology, serum chemistry, and urinalysis), and 12-lead ECGs. Documentation of AEs begins after baseline assessments are complete, prior to treatment with VALTOCO, and continue until follow-up visit. AEs may be either spontaneously reported or elicited during questioning and examination of a subject. AE information is elicited at study visits by indirect questioning using a non-leading question. Subjects receive a follow-up phone call approximately 7 days (±4 days) after the Day 180 visit to determine if any AE has occurred and to follow-up on any treatment-emergent AEs (TEAEs) ongoing since last communication with the subject.

Objective evaluations of nasal irritation is assessed by a trained observer after administration of the intranasal formulation. Nasal irritation is also evaluated prior to administration of intranasal diazepam (VALTOCO®) (baseline) and at 2 (±15 min), 4 (±30 min), and 6 (±30 min) hours post dose, and at discharge. Mucosal erythema, mucosal edema, nasal discharge, mucosal crusting and mucosal epistaxis are evaluated on separate scales prior to administration of intranasal diazepam (VALTOCO®) (baseline), at 30 (±10 min) minutes, and 1 (±10 min), 2 (±15 min), 4 (±30 min), and 6 (±30 min) hours post dose, and at discharge. Nasal irritation assessments are also performed on Day 30, Day 90, and Day 180 visits.

Safety data is summarized and descriptive statistics are provided for actual values and change from baseline values for physical and neurological examination including HEENT, vital signs, and clinical laboratory tests (serum chemistry, hematology, and urinalysis). The incidence and severity of TEAEs reported during the study and their relationship to study drug are tabulated. TEAEs are coded using the Medical Dictionary for Regulatory Activities (MedDRA) and are presented by body system.

The World Health Organization Drug Dictionary (WHODD) is used to classify prior and concomitant medications by therapeutic class and preferred term. Prior and concomitant medication usage is summarized by the number and percentage of subjects receiving each medication within each therapeutic class by dose cohort.

Following the single dose administration, a total of six (6) blood samples (3 mL each) for PK evaluation are collected from each subject at specific times depending on the block-permutated random sequence assigned:

A total of six (6) blood samples for PK evaluation are collected from each subject at specific times depending on sequence:

- Sequence 1: Pre-dose, 60, 120, 180, 240, and 360-minute time points
- Sequence 2: Pre-dose, 15, 75, 195, 300, and 360-minute time points
- Sequence 3: Pre-dose, 45, 90, 150, 210, and 360-minute time points A range of ±5 minutes is allowed for time points from 15 to 60 minutes and ±10 minutes for time points from 75 to 360 minutes. For all blood samples the actual time of collection is recorded and entered into the case report form (CRF).

The diazepam and desmethyldiazepam (metabolite) concentrations in the single-dose period are analyzed using model-independent methods to calculate PK parameters such as $C_{max}$, time to $C_{max}$ ($T_{max}$), and $AUC_{(0-6)}$. Other PK parameters are calculated, if needed. PK parameters are determined using actual times of sample collection relative to the administration of VALTOCO®. Concentrations below the limit of quantitation (BLQ) before the first quantifiable concentration are assigned a value of zero; other BLQ concentrations at any other time points are reported as missing.

Systemic exposure, measured by $C_{max}$ and $AUC_{(0-6)}$, are compared in subjects aged 2-5 years and subjects 6 years of age and older using two one-sided t-tests procedure. Confidence intervals (CI) (90%) are constructed for the geometric mean ratios (GMR) of the two parameters using the log-transformed data. In addition, plasma concentration data from this study are fitted to a previously developed population model for diazepam PK after administration of VALTOCO® in children (6-12 years) and adult subjects using NONMEM software (V 7.3, Icon Ltd). The relationship between diazepam PK parameters and age is evaluated. Additional covariates that may explain variability in exposure is investigated in this analysis. Exposure parameters in the 2-5-year-old population is compared to exposure with other pediatric age groups and in adults, if feasible.

Complete blood cell count (CBC) include red blood cell (RBC), RBC morphology, reticulocyte count, hemoglobin, hematocrit, white blood cell (WBC) with differential, and platelet count. Comprehensive metabolic panel include serum alkaline phosphatase, alanine aminotransferase (ALT), aspartate aminotransferase (AST), glucose, calcium, phosphorus, chloride, sodium, potassium, blood urea nitrogen (BUN), creatinine, total bilirubin, albumin, total protein, amylase, bicarbonate/carbon dioxide ($CO_2$), uric acid, and lactate dehydrogenase (LDH).

Urinalysis includes appearance, color, pH, specific gravity, glucose, protein, ketones, blood, creatinine clearance, and a detailed microscopic analysis. Microscopic analysis is performed regardless of macroscopic results and includes the following: WBC, RBC, cast/type, crystal/type, and bacteria. Standard urinalysis is conducted on the same day as blood chemistry.

Each subject participates in the study for approximately 208 days, which comprises a 21-day screening period, a single-dose treatment period, 180-day open-label safety period, and a follow-up phone call 7 days from Day 180.

The invention claimed is:

1. A method of treating intermittent, stereotypic episodes of frequent seizure activity that are distinct from a subject's usual seizure pattern in a pediatric subject that is 2 to 5 years old and 23 to 33 kg in body weight having epilepsy, said method comprising:

intranasally administering a pharmaceutical solution to the pediatric subject, wherein the pharmaceutical solution is one spray in each nostril of 100 μL of pharmaceutical solution having a diazepam concentration of 75 mg/mL, 0.25% w/v dodecyl maltoside, and a carrier system comprising 10.5% w/v benzyl alcohol;

wherein said administering is to a nasal mucosal membrane of the pediatric subject to treat the intermittent, stereotypic episodes of frequent seizure activity that are distinct from the subject's usual seizure pattern in the pediatric subject.

2. The method of claim 1, wherein the carrier system further comprises 56.5% w/V vitamin E and an amount of ethanol sufficient to reach a volume of 100 μL.

3. The method of claim 1, wherein the pharmaceutical solution is provided in a pre-primed single use dosage device.

4. The method of claim 1, wherein said administering reduces clinical seizure activity in the pediatric subject for a period of at least 48 hours after said administering.

5. The method of claim 1, wherein said administering prevents a second seizure in the pediatric subject for a period of at least 8 hours after said administering.

6. The method of claim 1, wherein said administering prevents a second seizure in the pediatric subject for a period of at least 48 hours after said administering.

7. The method of claim 1, wherein the pediatric subject does not require a second administration of said composition within at least 24-hours of experiencing a first seizure.

8. The method of claim 1, wherein the administering is performed in a prodromal phase or pre-ictal phase of a seizure.

9. The method of claim 1, wherein the administering is performed in an ictal phase of a seizure.

10. The method of claim 1, wherein said administering achieves 96% to 97% bioavailability of an equivalent dose of intravenously administered diazepam.

11. The method of claim 1, wherein the pharmaceutical solution is self-administered by the subject.

12. A method of treating intermittent, stereotypic episodes of frequent seizure activity that are distinct from a subject's usual seizure pattern in a pediatric subject that is 2 to 5 years old and 6 to 11 kg in body weight having epilepsy, said method comprising:

intranasally administering a pharmaceutical solution to the pediatric subject, wherein the pharmaceutical solution is one spray in a single nostril of 100 μL of the pharmaceutical solution having a diazepam concentration of 50 mg/mL, 0.25% w/v dodecyl maltoside and a carrier system comprising 10.5% w/v benzyl alcohol;

wherein said administering is to a nasal mucosal membrane of the pediatric subject to treat the intermittent, stereotypic episodes of frequent seizure activity that are distinct from the subject's usual seizure pattern in the pediatric subject.

13. The method of claim 12, wherein the carrier system further comprises 56.5% w/V vitamin E and an amount of ethanol sufficient to reach a volume of 100 μL.

14. The method of claim 12, wherein the pharmaceutical solution is provided in a pre-primed single use dosage device.

15. The method of claim 12, wherein said administering reduces clinical seizure activity in the pediatric subject for a period of at least 48 hours after said administering.

16. The method of claim 12, wherein said administering prevents a second seizure in the pediatric subject for a period of at least 8 hours after said administering.

17. The method of claim 12, wherein said administering prevents a second seizure in the pediatric subject for a period of at least 48 hours after said administering.

18. The method of claim 12, wherein the pediatric subject does not require a second administration of said composition within at least 24-hours of experiencing a first seizure.

19. The method of claim 12, wherein the administering is performed in a prodromal phase or pre-ictal phase of a seizure.

20. The method of claim 12, wherein the administering is performed in an ictal phase of a seizure.

21. The method of claim 12, wherein said administering achieves 96% to 97% bioavailability of an equivalent dose of intravenously administered diazepam.

22. The method of claim 12, wherein the pharmaceutical solution is self-administered by the subject.

23. A method of treating intermittent, stereotypic episodes of frequent seizure activity that are distinct from a subject's usual seizure pattern in a pediatric subject that is 2 to 5 years old and 12 to 22 kg in body weight having epilepsy, said method comprising:

intranasally administering a pharmaceutical solution to the pediatric subject, wherein the pharmaceutical solution one spray in a single nostril of 100 μL of the pharmaceutical solution having a diazepam concentration of 100 mg/mL, 0.25% w/v dodecyl maltoside and a carrier system comprising 10.5% w/v benzyl alcohol; and wherein said administering is to a nasal mucosal membrane of the pediatric subject to treat the intermittent, stereotypic episodes of frequent seizure activity that are distinct from the subject's usual seizure pattern in the pediatric subject.

24. The method of claim 23, wherein the carrier system further comprises 56.5% w/V vitamin E and an amount of ethanol sufficient to reach a volume of 100 μL.

25. The method of claim 23, wherein the pharmaceutical solution is provided in a pre-primed single use dosage device.

26. The method of claim 23, wherein said administering reduces clinical seizure activity in the pediatric subject for a period of at least 48 hours after said administering.

27. The method of claim 23, wherein said administering prevents a second seizure in the pediatric subject for a period of at least 8 hours after said administering.

28. The method of claim 23, wherein said administering prevents a second seizure in the pediatric subject for a period of at least 48 hours after said administering.

29. The method of claim 23, wherein the pediatric subject does not require a second administration of said composition within at least 24-hours of experiencing a first seizure.

30. The method of claim 23, wherein the administering is performed in a prodromal phase or pre-ictal phase of a seizure.

31. The method of claim 23, wherein the administering is performed in an ictal phase of a seizure.

32. The method of claim 23, wherein said administering achieves 96% to 97% bioavailability of an equivalent dose of intravenously administered diazepam.

33. The method of claim 23, wherein the pharmaceutical solution is self-administered by the subject.

* * * * *